United States Patent
Bae et al.

(10) Patent No.: US 10,342,667 B2
(45) Date of Patent: *Jul. 9, 2019

(54) ARTHROPLASTY SYSTEMS AND METHODS

(71) Applicant: ENGAGE MEDICAL HOLDINGS, LLC, Los Angeles, CA (US)

(72) Inventors: Hyun Bae, Santa Monica, CA (US); Edwin Su, New York, NY (US); Brady R. Shirley, Lewisville, TX (US); Joshua A. Butters, Chandler, AZ (US); Andrew R. Fauth, North Logan, UT (US); Daniel J. Triplett, Providence, UT (US); Neil Etherington, Smithfield, UT (US); Nicholas Slater, Chandler, AZ (US); Dylan M. Hushka, Longmont, CO (US); Carlyle J. Creger, Wellsville, UT (US); Ephraim Akyuz, Salt Lake City, UT (US); Daniel Hayes, Placerville, CA (US)

(73) Assignee: ENGAGE MEDICAL HOLDINGS, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/892,005

(22) Filed: Feb. 8, 2018

(65) Prior Publication Data

US 2018/0161167 A1 Jun. 14, 2018

Related U.S. Application Data

(63) Continuation of application No. 13/328,592, filed on Dec. 16, 2011, now Pat. No. 9,925,051.

(Continued)

(51) Int. Cl.
A61F 2/38 (2006.01)
A61F 2/46 (2006.01)
A61F 2/30 (2006.01)

(52) U.S. Cl.
CPC .......... *A61F 2/389* (2013.01); *A61F 2/30771* (2013.01); *A61F 2/3859* (2013.01);
(Continued)

(58) Field of Classification Search
CPC ........ A61F 2/3859; A61F 2/461; A61F 2/442; A61F 2/4455; A61F 2002/30387;
(Continued)

(56) References Cited

U.S. PATENT DOCUMENTS 3,486,505 A 12/1969 Morrison
3,641,590 A 2/1972 Michele
(Continued)

FOREIGN PATENT DOCUMENTS

EP 0179695 4/1986
EP 1327423 7/2003
(Continued)

*Primary Examiner* — Brian A Dukert
(74) *Attorney, Agent, or Firm* — Maywood IP Law; G. Jo Hays; David W. Meibos

(57) ABSTRACT

Systems for joint arthroplasty include prostheses which are secured to bone with sliding anchors. Examples include unicondylar and bicondylar knee prostheses for hemi-arthroplasty and total arthroplasty. Instruments guide the anchors into proper engagement with the prosthetic components. Methods of using the prostheses and instruments are disclosed.

17 Claims, 22 Drawing Sheets

Related U.S. Application Data

(60) Provisional application No. 61/423,827, filed on Dec. 16, 2010, provisional application No. 61/442,464, filed on Feb. 14, 2011, provisional application No. 61/450,753, filed on Mar. 9, 2011.

(52) U.S. Cl.
CPC .... *A61F 2/461* (2013.01); *A61F 2002/30383* (2013.01); *A61F 2002/30387* (2013.01); *A61F 2002/30398* (2013.01); *A61F 2002/30401* (2013.01); *A61F 2002/30841* (2013.01); *A61F 2002/30845* (2013.01); *A61F 2002/30848* (2013.01); *A61F 2002/30879* (2013.01); *A61F 2002/30884* (2013.01)

(58) Field of Classification Search
CPC .. A61F 2002/30398; A61F 2002/30401; A61F 2002/30841; A61F 2002/30845; A61F 2002/30884
See application file for complete search history.

(56) References Cited

U.S. PATENT DOCUMENTS

| | | |
|---|---|---|
| 3,650,309 A | 3/1972 | Neuschotz |
| 3,842,825 A | 10/1974 | Wagner |
| 3,848,276 A | 11/1974 | Martinez |
| 3,882,917 A | 5/1975 | Orlomoski |
| 3,896,504 A | 7/1975 | Fischer |
| 3,907,017 A | 9/1975 | Stanwick |
| 3,927,503 A | 12/1975 | Wilson |
| 4,011,602 A | 3/1977 | Rybicki |
| 4,047,524 A | 9/1977 | Hall |
| 4,260,005 A | 4/1981 | Stencel |
| 4,349,955 A | 9/1982 | Keen |
| 4,355,429 A | 10/1982 | Mittelmeier |
| 4,454,875 A | 6/1984 | Pratt |
| 4,484,570 A | 11/1984 | Sutter |
| 4,501,269 A | 2/1985 | Bagby |
| D281,814 S | 12/1985 | Pratt |
| 4,570,623 A | 2/1986 | Ellison |
| 4,611,581 A | 9/1986 | Steffee |
| 4,642,869 A | 2/1987 | Muller |
| 4,681,589 A | 7/1987 | Tronzo |
| 4,716,893 A | 1/1988 | Fischer |
| 4,743,256 A | 5/1988 | Brantigan |
| 4,743,262 A | 5/1988 | Tronzo |
| 4,764,067 A | 8/1988 | Kawashima |
| 4,820,305 A | 4/1989 | Harms |
| 4,834,757 A | 5/1989 | Brantigan |
| 4,838,891 A | 6/1989 | Branemark |
| 4,848,328 A | 7/1989 | Laboureau |
| 4,865,607 A | 9/1989 | Witzel |
| 4,874,389 A | 10/1989 | Downey |
| 4,930,962 A | 6/1990 | Reynolds |
| 4,946,378 A | 8/1990 | Hirayama |
| 4,957,496 A | 9/1990 | Schmidt |
| 5,002,576 A | 3/1991 | Fuhrmann |
| 5,019,103 A | 5/1991 | Van Zile |
| 5,053,038 A | 10/1991 | Sheehan |
| 5,074,880 A | 12/1991 | Mansat |
| 5,147,361 A | 9/1992 | Ojima |
| 5,163,960 A | 11/1992 | Bonutti |
| 5,192,324 A | 3/1993 | Kenna |
| 5,192,327 A | 3/1993 | Brantigan |
| 5,306,309 A | 4/1994 | Wagner |
| 5,314,477 A | 5/1994 | Marnay |
| 5,352,229 A | 10/1994 | Goble |
| 5,366,479 A | 11/1994 | McGarry |
| 5,431,658 A | 7/1995 | Moskovich |
| 5,443,515 A | 8/1995 | Cohen |
| 5,449,359 A | 9/1995 | Groiso |
| 5,454,814 A | 10/1995 | Comte |
| D364,462 S | 11/1995 | Michelson |
| 5,507,816 A | 4/1996 | Bullivant |
| 5,514,180 A | 5/1996 | Heggeness |
| D378,409 S | 3/1997 | Michelson |
| 5,609,635 A | 3/1997 | Michelson |
| 5,658,337 A | 8/1997 | Kohrs |
| 5,660,188 A | 8/1997 | Groiso |
| 5,683,394 A | 11/1997 | Rinner |
| 5,702,449 A | 12/1997 | McKay |
| 5,709,683 A | 1/1998 | Bagby |
| 5,713,899 A | 2/1998 | Marnay |
| 5,769,852 A | 6/1998 | Brånemark |
| 5,772,661 A | 6/1998 | Michelson |
| 5,776,199 A | 7/1998 | Michelson |
| 5,776,202 A | 7/1998 | Copf |
| 5,788,701 A | 8/1998 | McCue |
| 5,800,550 A | 9/1998 | Sertich |
| 5,853,414 A | 12/1998 | Groiso |
| 5,860,973 A | 1/1999 | Michelson |
| 5,885,287 A | 3/1999 | Bagby |
| 5,893,889 A | 4/1999 | Harrington |
| 5,893,890 A | 4/1999 | Pisharodi |
| 5,947,999 A | 9/1999 | Groiso |
| 5,993,476 A | 11/1999 | Groiso |
| 6,039,762 A | 3/2000 | McKay |
| 6,063,121 A | 5/2000 | Xavier |
| 6,080,155 A | 6/2000 | Michelson |
| 6,096,080 A | 8/2000 | Nicholson |
| 6,102,949 A | 8/2000 | Biedermann |
| 6,113,638 A | 9/2000 | Williams |
| 6,120,503 A | 9/2000 | Michelson |
| 6,136,001 A | 10/2000 | Michelson |
| 6,159,214 A | 12/2000 | Michelson |
| 6,224,607 B1 | 5/2001 | Michelson |
| 6,235,059 B1 | 5/2001 | Benezech |
| 6,241,769 B1 | 6/2001 | Nicholson |
| 6,241,770 B1 | 6/2001 | Michelson |
| 6,270,498 B1 | 8/2001 | Michelson |
| 6,302,914 B1 | 10/2001 | Michelson |
| 6,309,421 B1 | 10/2001 | Pisharodi |
| 6,325,805 B1 | 12/2001 | Ogilvie |
| 6,336,928 B1 | 1/2002 | Guerin |
| 6,364,880 B1 | 4/2002 | Michelson |
| 6,402,785 B1 | 6/2002 | Zdeblick |
| 6,413,278 B1 | 7/2002 | Marchosky |
| 6,432,107 B1 | 8/2002 | Ferree |
| 6,436,098 B1 | 8/2002 | Michelson |
| 6,447,524 B1 | 9/2002 | Knodel |
| 6,447,544 B1 | 9/2002 | Michelson |
| 6,447,546 B1 | 9/2002 | Bramlet |
| 6,458,159 B1 | 10/2002 | Thalgott |
| 6,478,800 B1 | 11/2002 | Fraser |
| 6,485,517 B1 | 11/2002 | Michelson |
| 6,506,216 B1 | 1/2003 | McCue |
| 6,537,320 B1 | 3/2003 | Michelson |
| 6,558,423 B1 | 5/2003 | Michelson |
| 6,558,424 B2 | 5/2003 | Thalgott |
| 6,582,468 B1 | 6/2003 | Gauchet |
| 6,599,294 B2 | 7/2003 | Fuss |
| 6,610,093 B1 | 8/2003 | Pisharodi |
| 6,620,198 B2 | 9/2003 | Burstein |
| 6,652,533 B2 | 11/2003 | O'Neil |
| 6,679,887 B2 | 1/2004 | Nicholson |
| 6,716,245 B2 | 4/2004 | Pasquet |
| 6,726,720 B2 | 4/2004 | Ross |
| 6,740,118 B2 | 5/2004 | Eisermann |
| 6,743,256 B2 | 6/2004 | Mason |
| 6,746,450 B1 | 6/2004 | Wall |
| 6,755,841 B2 | 6/2004 | Fraser |
| 6,767,356 B2 | 7/2004 | Kanner |
| 6,767,367 B1 | 7/2004 | Michelson |
| 6,770,074 B2 | 8/2004 | Michelson |
| 6,770,096 B2 | 8/2004 | Bolger |
| 6,773,437 B2 | 8/2004 | Ogilvie |
| 6,800,093 B2 | 10/2004 | Nicholson |
| 6,802,863 B2 | 10/2004 | Lawson |
| 6,827,740 B1 | 12/2004 | Michelson |
| 6,835,208 B2 | 12/2004 | Marchosky |
| 6,849,093 B2 | 2/2005 | Michelson |
| 6,875,213 B2 | 4/2005 | Michelson |

(56) References Cited

U.S. PATENT DOCUMENTS

| | | |
|---|---|---|
| 6,923,810 B1 | 8/2005 | Michelson |
| 6,923,830 B2 | 8/2005 | Michelson |
| 6,926,718 B1 | 8/2005 | Michelson |
| 6,942,698 B1 | 9/2005 | Jackson |
| 6,969,390 B2 | 11/2005 | Michelson |
| 6,972,035 B2 | 12/2005 | Michelson |
| 6,981,975 B2 | 1/2006 | Michelson |
| 6,989,031 B2 | 1/2006 | Michelson |
| 7,033,394 B2 | 4/2006 | Michelson |
| 7,041,135 B2 | 5/2006 | Michelson |
| 7,044,972 B2 | 5/2006 | Mathys, Jr. |
| 7,048,766 B2 | 5/2006 | Ferree |
| 7,056,344 B2 | 6/2006 | Huppert |
| 7,056,345 B2 | 6/2006 | Kuslich |
| 7,060,097 B2 | 6/2006 | Fraser |
| 7,066,961 B2 | 6/2006 | Michelson |
| 7,083,623 B2 | 8/2006 | Michelson |
| 7,083,652 B2 | 8/2006 | McCue |
| 7,087,082 B2 | 8/2006 | Paul |
| 7,112,206 B2 | 9/2006 | Michelson |
| 7,115,146 B2 | 10/2006 | Boyer, II |
| 7,118,580 B1 | 10/2006 | Beyersdorff |
| 7,128,761 B2 | 10/2006 | Kuras |
| 7,163,560 B2 | 1/2007 | Mason |
| 7,166,110 B2 | 1/2007 | Yundt |
| 7,166,129 B2 | 1/2007 | Michelson |
| 7,169,182 B2 | 1/2007 | Errico |
| 7,204,852 B2 | 4/2007 | Marnay |
| 7,235,101 B2 | 6/2007 | Berry |
| 7,235,105 B2 | 6/2007 | Jackson |
| 7,255,698 B2 | 8/2007 | Michelson |
| 7,320,707 B2 | 1/2008 | Zucherman |
| 7,326,248 B2 | 2/2008 | Michelson |
| 7,331,995 B2 | 2/2008 | Eisermann |
| 7,357,817 B2 | 4/2008 | D'Alessio, II |
| 7,364,589 B2 | 4/2008 | Eisermann |
| 7,396,365 B2 | 7/2008 | Michelson |
| 7,462,196 B2 | 12/2008 | Fraser |
| 7,481,830 B2 | 1/2009 | Wall |
| 7,481,832 B1 | 1/2009 | Meridew |
| D586,915 S | 2/2009 | Grim |
| 7,491,205 B1 | 2/2009 | Michelson |
| 7,503,933 B2 | 3/2009 | Michelson |
| 7,503,934 B2 | 3/2009 | Eisermann |
| 7,503,935 B2 | 3/2009 | Zucherman |
| D594,986 S | 6/2009 | Miles |
| 7,540,882 B2 | 6/2009 | Michelson |
| 7,556,650 B2 | 7/2009 | Collins |
| 7,572,293 B2 | 8/2009 | Rhodes |
| 7,588,600 B2 | 9/2009 | Benzel |
| 7,594,931 B2 | 9/2009 | Louis |
| 7,611,538 B2 | 11/2009 | Belliard |
| 7,658,766 B2 | 2/2010 | Melkent |
| 7,695,516 B2 | 4/2010 | Zeegers |
| 7,749,271 B2 | 7/2010 | Fischer |
| 7,763,076 B2 | 7/2010 | Navarro |
| 7,780,676 B2 | 8/2010 | Lakin |
| 7,837,732 B2 | 11/2010 | Zucherman |
| 7,850,791 B2 | 12/2010 | Quadakkers |
| 7,883,510 B2 | 2/2011 | Kim |
| 7,887,563 B2 | 2/2011 | Cummins |
| 7,896,919 B2 | 3/2011 | Belliard |
| 7,909,871 B2 | 3/2011 | Abdou |
| 7,918,891 B1 | 4/2011 | Curran |
| 7,966,799 B2 | 6/2011 | Morgan |
| 8,021,403 B2 | 9/2011 | Wall |
| 8,034,076 B2 | 10/2011 | Criscuolo |
| 8,062,297 B2 | 11/2011 | Faillace et al. |
| 8,100,972 B1 | 1/2012 | Bruffey |
| 8,100,974 B2 | 1/2012 | Duggal |
| 8,105,389 B2 | 1/2012 | Berelsman |
| 8,123,757 B2 | 2/2012 | Zalenski |
| 8,133,283 B2 | 3/2012 | Wilson |
| 8,157,865 B2 | 4/2012 | Hochschuler |
| 8,491,598 B2 | 7/2013 | Crook |
| 8,500,747 B2 | 8/2013 | DeRidder |
| 8,636,191 B2 | 1/2014 | Meagher |
| 8,747,412 B2 | 6/2014 | Bae |
| 8,808,294 B2 | 8/2014 | Fox |
| 9,254,130 B2 | 2/2016 | Hollis |
| 9,480,511 B2 | 11/2016 | Butters |
| 2001/0000532 A1 | 4/2001 | Michelson |
| 2001/0010001 A1 | 7/2001 | Michelson |
| 2001/0010002 A1 | 7/2001 | Michelson |
| 2001/0010020 A1 | 7/2001 | Michelson |
| 2001/0037154 A1 | 11/2001 | Martin |
| 2001/0047207 A1 | 11/2001 | Michelson |
| 2001/0047208 A1 | 11/2001 | Michelson |
| 2002/0004683 A1 | 1/2002 | Michelson |
| 2002/0035400 A1 | 3/2002 | Bryan |
| 2002/0049447 A1 | 4/2002 | Li |
| 2002/0091390 A1 | 7/2002 | Michelson |
| 2002/0095155 A1 | 7/2002 | Michelson |
| 2002/0099376 A1 | 7/2002 | Michelson |
| 2002/0099378 A1 | 7/2002 | Michelson |
| 2002/0116065 A1 | 8/2002 | Jackson |
| 2002/0116165 A1 | 8/2002 | El Ghoroury |
| 2002/0147454 A1 | 10/2002 | Neto |
| 2002/0147499 A1 | 10/2002 | Shea |
| 2002/0161443 A1 | 10/2002 | Michelson |
| 2002/0165613 A1 | 11/2002 | Lin |
| 2003/0023307 A1 | 1/2003 | Michelson |
| 2003/0045940 A1 | 3/2003 | Eberlein |
| 2003/0060884 A1 | 3/2003 | Fell |
| 2003/0120344 A1 | 6/2003 | Michelson |
| 2003/0149483 A1 | 8/2003 | Michelson |
| 2003/0158553 A1 | 8/2003 | Michelson |
| 2003/0195517 A1 | 10/2003 | Michelson |
| 2003/0195561 A1 | 10/2003 | Carley |
| 2003/0195632 A1 | 10/2003 | Foley |
| 2004/0030336 A1 | 2/2004 | Khanna |
| 2004/0030339 A1 | 2/2004 | Wack |
| 2004/0064185 A1 | 4/2004 | Michelson |
| 2004/0073315 A1 | 4/2004 | Justin |
| 2004/0083005 A1* | 4/2004 | Jacobsson ............... A61F 2/389 623/23.44 |
| 2004/0117018 A1 | 6/2004 | Michelson |
| 2004/0122518 A1 | 6/2004 | Rhoda |
| 2004/0133203 A1 | 7/2004 | Young |
| 2004/0148028 A1 | 7/2004 | Ferree |
| 2004/0176853 A1 | 9/2004 | Sennett |
| 2004/0210313 A1 | 10/2004 | Michelson |
| 2004/0210314 A1 | 10/2004 | Michelson |
| 2004/0215203 A1 | 10/2004 | Michelson |
| 2004/0220668 A1 | 11/2004 | Eisermann |
| 2004/0220670 A1 | 11/2004 | Eisermann |
| 2004/0225295 A1 | 11/2004 | Zubok |
| 2004/0230308 A1 | 11/2004 | Michelson |
| 2004/0249388 A1 | 12/2004 | Michelson |
| 2004/0254581 A1 | 12/2004 | Leclair |
| 2004/0254644 A1 | 12/2004 | Taylor |
| 2004/0260286 A1 | 12/2004 | Ferree |
| 2005/0004672 A1 | 1/2005 | Pafford |
| 2005/0014919 A1 | 1/2005 | Hatakeyama |
| 2005/0027300 A1 | 2/2005 | Hawkins |
| 2005/0038512 A1 | 2/2005 | Michelson |
| 2005/0038513 A1 | 2/2005 | Michelson |
| 2005/0043802 A1 | 2/2005 | Eisermann |
| 2005/0049600 A1 | 3/2005 | Groiso |
| 2005/0055031 A1 | 3/2005 | Lim |
| 2005/0125065 A1 | 6/2005 | Zucherman |
| 2005/0131545 A1 | 6/2005 | Chervitz |
| 2005/0143747 A1 | 6/2005 | Zubok |
| 2005/0149192 A1 | 7/2005 | Zucherman |
| 2005/0165408 A1 | 7/2005 | Puno |
| 2005/0171606 A1 | 8/2005 | Michelson |
| 2005/0171607 A1 | 8/2005 | Michelson |
| 2005/0177239 A1 | 8/2005 | Steinberg |
| 2005/0187629 A1 | 8/2005 | Michelson |
| 2005/0192586 A1 | 9/2005 | Zucherman |
| 2005/0216089 A1 | 9/2005 | Michelson |
| 2005/0234555 A1 | 10/2005 | Sutton |
| 2005/0273108 A1 | 12/2005 | Groiso |
| 2006/0004453 A1 | 1/2006 | Bartish |

(56) References Cited

U.S. PATENT DOCUMENTS

| | | |
|---|---|---|
| 2006/0058802 A1 | 3/2006 | Kofoed |
| 2006/0074421 A1 | 4/2006 | Bickley |
| 2006/0079961 A1 | 4/2006 | Michelson |
| 2006/0085071 A1 | 4/2006 | Lechmann |
| 2006/0095136 A1 | 5/2006 | McLuen |
| 2006/0111787 A1 | 5/2006 | Bailie |
| 2006/0116769 A1 | 6/2006 | Marnay |
| 2006/0122702 A1 | 6/2006 | Michelson |
| 2006/0129238 A1 | 6/2006 | Paltzer |
| 2006/0136061 A1 | 6/2006 | Navarro |
| 2006/0142860 A1 | 6/2006 | Navarro |
| 2006/0149377 A1 | 7/2006 | Navarro |
| 2006/0149384 A1 | 7/2006 | Navarro |
| 2006/0167461 A1 | 7/2006 | Hawkins |
| 2006/0178745 A1 | 8/2006 | Bartish |
| 2006/0195097 A1 | 8/2006 | Evans |
| 2006/0212123 A1 | 9/2006 | Lechmann |
| 2006/0241641 A1 | 10/2006 | Albans |
| 2006/0259143 A1 | 11/2006 | Navarro |
| 2006/0259145 A1 | 11/2006 | Navarro |
| 2007/0010890 A1 | 1/2007 | Collazo |
| 2007/0050032 A1 | 3/2007 | Gittings |
| 2007/0055376 A1 | 3/2007 | Michelson |
| 2007/0073404 A1 | 3/2007 | Rashbaum |
| 2007/0093839 A1 | 4/2007 | Beckendorf |
| 2007/0106388 A1 | 5/2007 | Michelson |
| 2007/0118132 A1 | 5/2007 | Culbert |
| 2007/0123903 A1 | 5/2007 | Raymond |
| 2007/0142922 A1 | 6/2007 | Lewis |
| 2007/0185375 A1 | 8/2007 | Stad |
| 2007/0233244 A1 | 10/2007 | Lopez |
| 2007/0239278 A1 | 10/2007 | Heinz |
| 2007/0288005 A1 | 12/2007 | Arnin |
| 2007/0288021 A1 | 12/2007 | Rickels |
| 2007/0299529 A1 | 12/2007 | Rhodes |
| 2008/0051901 A1 | 2/2008 | de Villiers |
| 2008/0051902 A1 | 2/2008 | Dwyer |
| 2008/0103598 A1 | 5/2008 | Trudeau |
| 2008/0108997 A1 | 5/2008 | Berrevoets |
| 2008/0132949 A1 | 6/2008 | Aferzon |
| 2008/0140208 A1 | 6/2008 | Zucherman |
| 2008/0147203 A1 | 6/2008 | Cronin |
| 2008/0154377 A1 | 6/2008 | Voellmicke |
| 2008/0167721 A1 | 7/2008 | Bao |
| 2008/0177275 A1 | 7/2008 | Wing |
| 2008/0208345 A1 | 8/2008 | Hurlbert |
| 2008/0249575 A1 | 10/2008 | Waugh |
| 2008/0249623 A1 | 10/2008 | Bao |
| 2008/0269764 A1 | 10/2008 | Blain |
| 2008/0275455 A1 | 11/2008 | Berry |
| 2008/0287957 A1 | 11/2008 | Hester |
| 2009/0005784 A1 | 1/2009 | Blain |
| 2009/0005870 A1 | 1/2009 | Hawkins |
| 2009/0048604 A1 | 2/2009 | Milz |
| 2009/0062921 A1 | 3/2009 | Michelson |
| 2009/0088849 A1 | 4/2009 | Armstrong |
| 2009/0099601 A1 | 4/2009 | Aferzon |
| 2009/0099602 A1 | 4/2009 | Aflatoon |
| 2009/0164020 A1 | 6/2009 | Janowski |
| 2009/0209967 A1 | 8/2009 | Evans |
| 2009/0240333 A1 | 9/2009 | Trudeau |
| 2010/0004747 A1 | 1/2010 | Lin |
| 2010/0069958 A1 | 3/2010 | Sullivan |
| 2010/0185287 A1 | 7/2010 | Allard |
| 2010/0201739 A1 | 8/2010 | Yamaguchi |
| 2010/0204737 A1 | 8/2010 | Bae |
| 2010/0204739 A1* | 8/2010 | Bae ................ A61B 17/846 606/300 |
| 2011/0022176 A1 | 1/2011 | Zucherman |
| 2011/0098819 A1 | 4/2011 | Eisermann |
| 2011/0160766 A1 | 6/2011 | Hendren |
| 2011/0160866 A1 | 6/2011 | Laurence |
| 2011/0166608 A1 | 7/2011 | Duggal |
| 2012/0191204 A1 | 7/2012 | Bae |
| 2012/0215315 A1 | 8/2012 | Hochschuler |
| 2012/0253406 A1 | 10/2012 | Bae |
| 2012/0265259 A1 | 10/2012 | LaPosta |
| 2012/0283837 A1* | 11/2012 | Bae ................ A61F 2/447 623/17.16 |
| 2013/0013006 A1 | 1/2013 | Rashbaum |
| 2013/0267956 A1 | 10/2013 | Terrill |
| 2014/0039632 A1 | 2/2014 | Hollis |
| 2016/0157906 A1 | 6/2016 | Hollis |
| 2017/0042576 A1 | 2/2017 | Butters |

FOREIGN PATENT DOCUMENTS

| | | |
|---|---|---|
| EP | 1827318 | 9/2007 |
| EP | 1872746 | 1/2008 |
| EP | 1897517 | 3/2008 |
| EP | 1983941 | 10/2008 |
| EP | 2651341 | 10/2013 |
| EP | 2685938 | 8/2015 |
| EP | 3178448 | 6/2017 |
| WO | WO1993022990 | 11/1993 |
| WO | WO2000025707 | 5/2000 |
| WO | WO2000064360 | 11/2000 |
| WO | WO2001003570 | 1/2001 |
| WO | WO2002003885 | 1/2002 |
| WO | WO2002058593 | 8/2002 |
| WO | WO2003005939 | 1/2003 |
| WO | WO2003039400 | 5/2003 |
| WO | WO2003053290 | 7/2003 |
| WO | WO2003065930 | 8/2003 |
| WO | WO2003092507 | 11/2003 |
| WO | WO2004071359 | 8/2004 |
| WO | WO2004080355 | 9/2004 |
| WO | WO2004089240 | 10/2004 |
| WO | WO2004100815 | 12/2004 |
| WO | WO2005051243 | 6/2005 |
| WO | WO2005074841 | 8/2005 |
| WO | WO2006051547 | 5/2006 |
| WO | WO2006074414 | 7/2006 |
| WO | WO2006086494 | 8/2006 |
| WO | WO2006120505 | 11/2006 |
| WO | WO2006122194 | 11/2006 |
| WO | WO2007028098 | 3/2007 |
| WO | WO2007034310 | 3/2007 |
| WO | WO2007087366 | 8/2007 |
| WO | WO2008014258 | 1/2008 |
| WO | WO2008014453 | 1/2008 |
| WO | WO2008021955 | 2/2008 |
| WO | WO2008034140 | 3/2008 |
| WO | WO2008128367 | 10/2008 |
| WO | WO2009070721 | 6/2009 |
| WO | WO2010039026 | 4/2010 |
| WO | WO2010121002 | 10/2010 |
| WO | WO2011044879 | 4/2011 |
| WO | WO2011090508 | 7/2011 |
| WO | WO2012083205 | 6/2012 |
| WO | WO2012112598 | 8/2012 |

* cited by examiner

ARTHROPLASTY SYSTEMS AND METHODS

CROSS-REFERENCE TO RELATED APPLICATIONS

This application is a continuation of:

U.S. patent application Ser. No. 13/328,592, filed Dec. 16, 2011, entitled ARTHROPLASTY SYSTEMS AND METHODS, which is pending.

U.S. patent application Ser. No. 13/328,592 claims the benefit of:

U.S. Provisional Patent Application No. 61/423,827, filed Dec. 16, 2010, entitled TIBIAL TRAY FIXATION;

U.S. Provisional Patent Application No. 61/442,464, filed Feb. 14, 2011, entitled SYSTEM AND METHOD FOR TIBIAL TRAY FIXATION; and U.S. Provisional Patent Application No. 61/450,753, filed Mar. 9, 2011, entitled FEMORAL AND HEMI-ARTHROPLASTY FIXATION USING ANCHOR TECHNOLOGY.

The above referenced documents are hereby incorporated by reference in their entirety.

BACKGROUND OF THE INVENTION

This disclosure relates to systems and methods for joint resurfacing, replacement, and the like. While the examples in the present disclosure relate to the knee joint, the systems and methods are applicable to other synovial joints in the body.

Arthroplasty procedures seek to replace a natural joint that has deteriorated in its functionality, range of motion, weight bearing, and most, if not all, other performance and a lifestyle attributes. Joint resurfacing typically involves removal of at least a portion of a natural articular surface of a bone in order to replace the removed tissue with a prosthesis having an articular surface that replicates at least the removed portion of the natural articular surface. Joint replacement may involve more extensive bone removal and subsequent replacement with a more substantial prosthesis. In this disclosure, remarks about resurfacing are to be considered equally relevant to replacement, and vice versa.

Arthroplasty procedures may involve one or more articular surfaces of a joint. In the knee, for example, the medial femoral condyle, the lateral femoral condyle, the medial tibial condyle, the lateral tibial condyle, the trochlear groove, and/or the patella may be resurfaced or replaced. A procedure may be described as unicondylar if one condyle of the joint is treated, such as the medial tibial condyle. Bicondylar procedures may treat two condyles of a bone, such as the medial and lateral tibial condyles. A procedure may be described as unicompartmental if one compartment of the joint is treated, such as the medial compartment of the knee. Bicompartmental procedures may treat two compartments, such as the medial and lateral compartments of the knee. A procedure may be described as a total joint procedure if most or all opposing articular surfaces of the joint are resurfaced or replaced. A procedure may be described as a hemiarthroplasty procedure if the prosthetic component articulates against an opposing natural articular surface, such as the prosthetic medial tibial component articulating against the natural medial femoral condyle.

BRIEF DESCRIPTION OF THE DRAWINGS

Various examples of the present technology will now be discussed with reference to the appended drawings. It is appreciated that these drawings depict only typical examples of the invention and are therefore not to be considered limiting of its scope.

DETAILED DESCRIPTION

Figure 1:
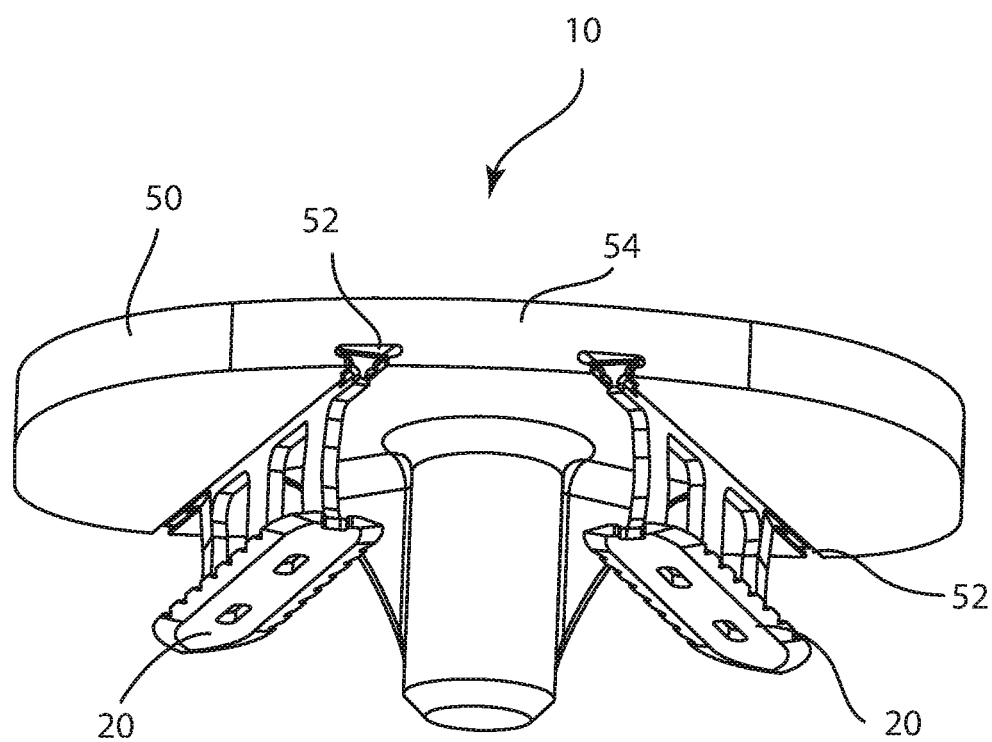
FIG. 1 is a bottom perspective view of a knee tibial prosthesis with a bicondylar tibial component and fixation elements.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

In this specification, standard knee anatomical terms are employed with their ordinary and customary meanings.

An example of a joint arthroplasty system includes a prosthetic articular surface which replaces at least a portion of a natural articular surface of a bone and a prosthetic component including a bone-contacting surface. The bone-contacting surface includes at least one undercut channel extending across at least a portion of the bone-contacting surface and through a perimeter edge of the bone-contacting surface. The system also includes an anchor with a rail, a blade, and a support. The rail has at least one lateral protrusion. The blade is offset from the rail. The support connects the rail and the blade. The rail is insertable into the channel to connect the anchor to the prosthetic component. When the rail is inserted into the channel, the lateral protrusion plastically deforms, the support protrudes through the bone-contacting surface, and the blade is carried at a distance from the bone-contacting surface.

In other examples of this system, the prosthetic component may be selected from the group consisting of a knee tibial component, a knee femoral component, and a knee patellar component. The prosthetic articular surface may be opposite the bone-contacting surface. A transverse cross section of the channel and a transverse cross section of the rail may be complementary negative and positive shapes, respectively. The blade may be inclined at an acute angle relative to the bone-contacting surface when the rail is in the channel. A leading end of the anchor may include oblique sharpened edges. The channel may include at least one shoulder formed in an edge of the channel, wherein the shoulder deforms the lateral protrusion when the rail is inserted into the channel.

Another example of a knee arthroplasty system includes a prosthetic articular surface which replaces at least a portion of a natural articular surface of a knee joint and a bone-contacting surface. The bone-contacting surface includes at least one undercut channel extending across at least a portion of the bone-contacting surface and through a perimeter edge of the bone-contacting surface. The system also includes an anchor with a rail, a blade, and a support. The blade is offset from the rail. The support connects the rail and the blade. The rail is insertable into the channel to connect the anchor to the prosthetic component. When the rail is inserted into the channel, the support protrudes through the bone-contacting surface, and the blade is carried at a distance from the bone-contacting surface.

In other examples of this system, the articular and bone-contacting surfaces may be carried by a prosthesis selected from the group consisting of a knee tibial prosthesis, a knee femoral prosthesis, and a knee patellar prosthesis. The prosthesis may be selected from the group consisting of a unicondylar prosthesis and a bicondylar prosthesis. A transverse cross section of the channel and a transverse cross section of the rail may be complementary negative and positive dovetail shapes, respectively. The blade may be inclined at an acute angle relative to the bone-contacting surface when the rail is in the channel. A leading end of the anchor may include oblique sharpened edges. When the rail is inserted into the channel, the rail may seize in the channel.

An example of a method of preparing a joint arthroplasty prosthesis for replacing at least a portion of a natural articular surface of a synovial joint includes providing a prosthesis with a bone-contacting surface and an articular surface, the bone-contacting surface including at least one undercut channel extending across at least a portion of the bone-contacting surface and through a perimeter edge of the bone-contacting surface, the articular surface replicating at least a portion of a natural articular surface of a synovial joint; providing an anchor including a rail, a blade, and a support, the rail including at least one laterally protruding tab, the blade offset from the rail, the support connecting the rail and the blade; sliding the rail into the channel, wherein the tab plastically deforms as the rail slides into the channel; and sliding a portion of the support into the channel, the support protruding through the bone-contacting surface, wherein a portion of the bone-contacting surface is spaced between the blade and the rail when the rail and the support are in the channel.

In other examples of this method, sliding the rail into the channel may be performed before sliding the portion of the support into the channel. Sliding the rail into the channel may include sliding the tab past a shoulder formed in an edge of the channel. The shoulder may deform the tab. The blade may be inclined at an acute angle relative to the bone-contacting surface when the rail is in the channel. The acute angle may open toward a leading end of the anchor. The method may also include providing a guide tool including an attachment portion and a guidance portion. The attachment portion may be releasably attachable to a portion of the prosthesis. The guidance portion may include at least one track. The method may also include attaching the attachment portion to the prosthesis. The track may coaxially align with the channel when the attachment portion is attached to the prosthesis. The method may also include inserting the rail into the track and sliding the anchor toward the prosthesis. Attaching the attachment portion to the prosthesis may include attaching a clip to the attachment portion and snapping the clip to the prosthesis.

Another example of a method of replacing at least a portion of a natural articular surface of a synovial joint includes forming a resection surface on a bone of the synovial joint to remove at least a portion of the natural articular surface of the bone; positioning a bone-contacting surface of a prosthesis against the resection surface; positioning an articular surface of the prosthesis to replace the removed natural articular surface; and installing an anchor to fix the prosthesis to the bone. Installing the anchor includes sliding a rail of the anchor into an undercut channel of the prosthesis, the channel extending through a perimeter edge of the bone-contacting surface and across at least a portion of the bone-contacting surface, wherein a laterally protruding tab of the rail plastically deforms as the rail slides into the channel; sliding a blade of the anchor into the bone, wherein portions of the bone-contacting surface and the resection surface become situated between the blade and the rail portion as the blade slides into the bone; and sliding a support of the anchor into the channel and the bone, the support connecting the blade to the rail.

In other examples of this method, sliding the rail into the channel may be performed before sliding the blade into the bone, which may be performed before sliding the support into the channel and the bone. Sliding the rail into the channel may include sliding the tab past a shoulder formed in an edge of the channel, wherein the shoulder deforms the tab. The blade may be inclined at an acute angle relative to the bone-contacting surface when the rail is in the channel, wherein the acute angle opens toward a leading end of the anchor. The method may also include providing a guide tool including an attachment portion and a guidance portion, the attachment portion releasably attachable to a portion of the prosthesis, the guidance portion including at least one track; attaching the attachment portion to the prosthesis, wherein the track coaxially aligns with the channel when the attachment portion is attached to the prosthesis; inserting the rail into the track; and sliding the anchor toward the prosthesis. Attaching the attachment portion to the prosthesis may include attaching a clip to the attachment portion and snapping the clip to the prosthesis.

This disclosure relates to systems and methods for joint resurfacing, replacement, and the like. This disclosure sets forth examples of joint prostheses with adjunctive fixation elements, or anchors. The anchors may contribute to initial and/or long term fixation of a prosthetic component to bone. The fixation elements may provide fixation alone, or in combination with other fixation means, such as bone cement or biological fixation to porous coating, to name just two examples. Each fixation element may be inserted into a complementary slot in the prosthetic component so that the fixation element protrudes from the prosthetic component into the adjacent bone. The fixation elements may be used in lieu of bone screws for component fixation.

Referring to FIG. 1, a knee tibial prosthesis 10 includes a tibial component 50 and at least one fixation element 20. The tibial component 50 may be referred to as a tibial tray 50. The tibial prosthesis 10 of FIG. 1 includes two fixation elements 20, which may also be referred to as anchors 20. The anchors 20 may be inserted from an anterior edge 54 of the tibial tray 50 and may be oriented roughly anterior-posterior, as shown. The anchors 20 may be parallel or angled relative to one another and/or the tray 50. For example, the anchors 20 of FIG. 1 are angled relative to one another, with the anchors closest together at the anterior edge 54 of the tibial tray 50. The anchors may also be tilted with respect to the tray 50, for example, tilted laterally. The anchors 20 are inserted in channels 52 in the tibial tray 50. The channels may be dovetailed as shown; other undercut channel geometries are contemplated, such as T-slots. The channels 52 of FIG. 1 extend between anterior and posterior edges 54, 66 of the tray 50. In some embodiments, the channels may only open at one of the anterior and posterior edges 54, 66, and may terminate in the main body of the tray 50. In other examples, the channels 52 may be oriented exactly anterior-posterior, exactly medial-lateral, roughly medial-lateral, or in another orientation. A channel 52 may open through any perimeter edge of a bone-contacting side 56 of the tray 50.

The anchors in the present disclosure may share some or all of the features of the anchors disclosed in U.S. patent application Ser. No. 12/640,892 to Bae, et al., which is incorporated by reference herein in its entirety.

Figure 2A:
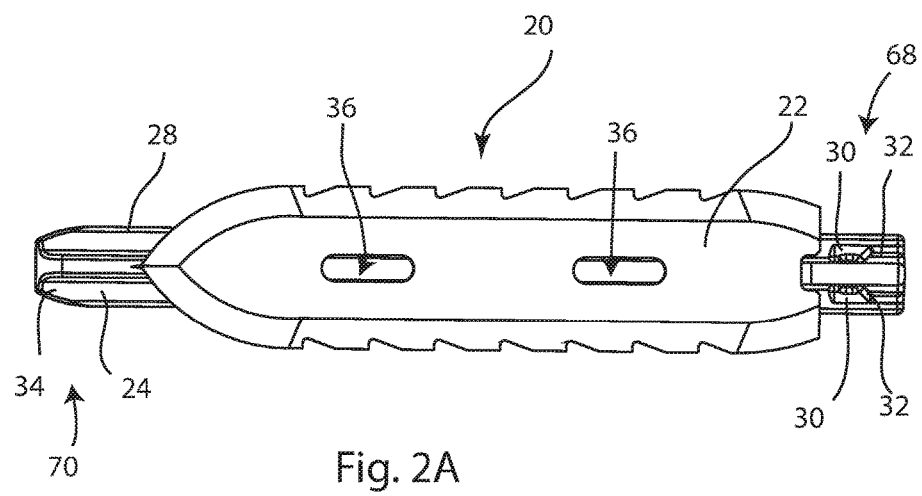
FIG. 2A is a top view of one of the fixation elements of FIG. 1.
Figure 2B:
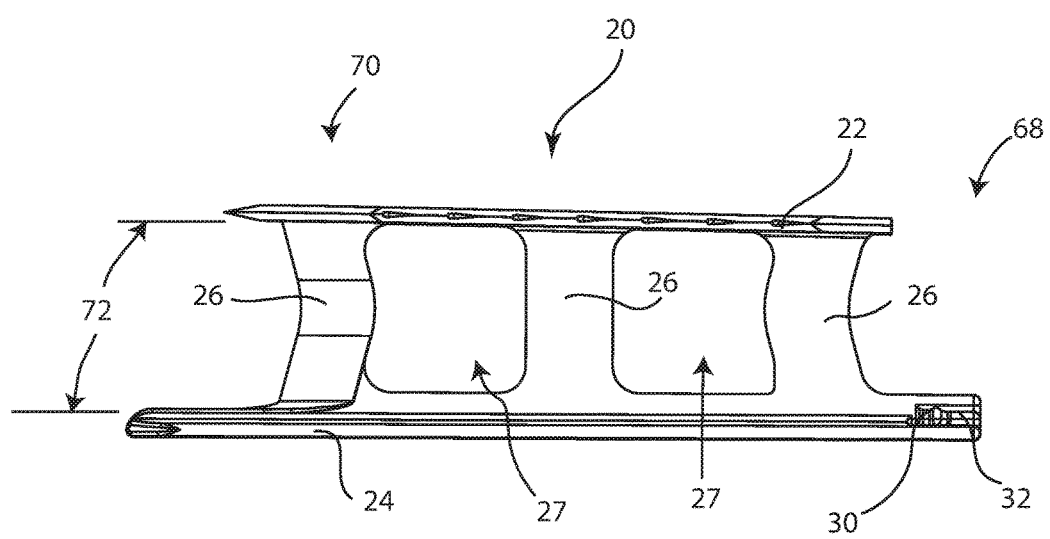
FIG. 2B is a side view of the fixation element of FIG. 2A.

Referring to FIGS. 2A and 2B, each fixation element or anchor 20 comprises a blade 22 and a rail 24. The blade and rail extend between a leading end 70 and a trailing end 68 of the anchor. The leading end 70 may also be referred to as a distal end 70; the trailing end 68 may also be referred to as a proximal end 68. Supports 26 connect the blade 22 to the rail 24. FIGS. 2A and 2B illustrate an anchor 20 with three supports 26, although other examples may include any number of supports. The supports 26 define apertures 27 through the anchor 20. In use, the blade 22 and at least a portion of the supports 26 may be inserted into bone. The blade 22 may be pointed, sharpened, and/or serrated, for ease of insertion into bone. The supports 26 may also be sharpened and/or obliquely profiled for ease of insertion into bone. The blade edges may be beveled. The blade 22 may be pierced by one or more apertures 36. Longitudinal edges 28 of the rail may be sized and shaped for complementary engagement with the dovetail channels 52 of the tray 50. In other examples, the rail may be of a complementary size and shape to engage another undercut channel geometry.

There may be a small tab 30 projecting from the rail 24. The tab may be said to protrude laterally or transversely from the rail 24. The tab deforms as the anchor is driven into the tibial tray 50, creating an interference fit. This material deformation serves to take up any relative motion between the anchor and the tibial tray as well as to lock the anchor 20 into the tray 50. The deformation may be characterized as plastic deformation, which may be at least partially irreversible. The deformation may cause galling, spot welding, and/or seizing to occur between the tab and the channel 52. Any of these adhesive phenomena may lock the anchor to the tray. There may be a physical stop 32 on the anchor to prevent over-insertion. A distal tip 34 of the anchor rail may be tapered for ease of insertion into, and movement along, the channels 52. In FIGS. 2A and 2B, tabs 30 are located on each side of the rail near the proximal end 68 and physical stops 32 are immediately proximal to each interference tab 30. Another example may include a tab 30 on only one side of the rail. Other examples may include multiple interference tabs 30 along the length of the rail 24. This arrangement may provide even greater fixation along the length of the anchor in the channel 52. Also, in other embodiments the length, height, or other dimensions of the anchor may vary.

To achieve optimal compression between the bone and the tibial tray, the anchor blade 22 may be angled divergent from the rail 24. At the leading, distal end 70 of the anchor 20, the blade 22 and the rail 24 may be farther apart than they are at the trailing, proximal end 68 of the anchor. The divergence angle 72 may be less than about 90 degrees. In some examples, the divergence angle may be less than about 15 degrees, less than about 5 degrees, or less than about 2 degrees. In the embodiment shown, the divergence angle between the blade 22 and the rail 24 is 1 degree. Divergence angles of less than 1 degree are also contemplated.

When the anchor rail 24 is inserted into the channel 52 of the tibial tray 50, the anchor blade 22 may diverge from an inferior or bone-contacting side 56 of the tray 50 at the same angle 72. Alternatively, the blade 22 may diverge from the inferior or bone-contacting side of the tray 50 at another angle, which may be greater than or less than the blade-to-rail divergence angle 72. Furthermore, the blade-to-tray divergence angle may open in the same or opposite direction as the blade-to-rail divergence angle 72.

The angle 72 between the blade 22 and the rail 24, and/or the angle between the blade and the bone-contacting side 56 may correlate to the mechanical properties of the bone into which the anchor 20 will be inserted, the desired amount of compression between the bone and the bone-contacting side, the compliance of the bone-contacting side, and/or other factors. For example, larger divergence angles may be appropriate for conditions such as: softer bone, greater compression, and/or a compliant bone-contacting side; smaller divergence angles may be appropriate for conditions such as harder or stiffer bone, less compression, and/or an unyielding bone-contacting side. The divergence angle may also correlate to the length of the anchor 20, with greater divergence angles possible with shorter anchors and smaller divergence angles suitable for longer anchors.

Figure 3A:
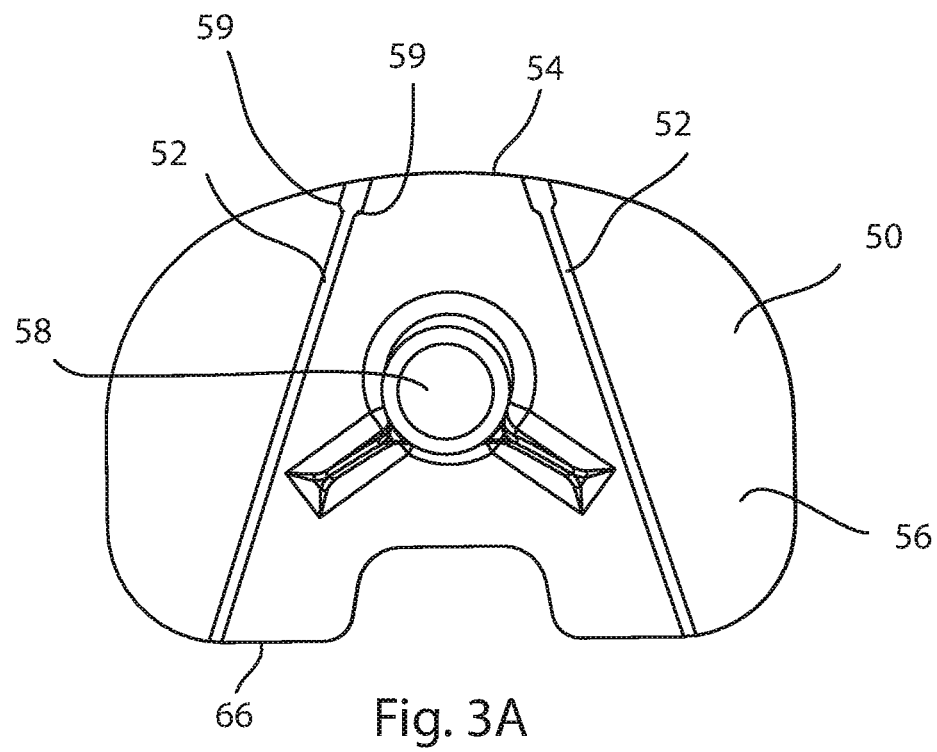
FIG. 3A is a bottom view of the tibial component of FIG. 1.
Figure 3B:
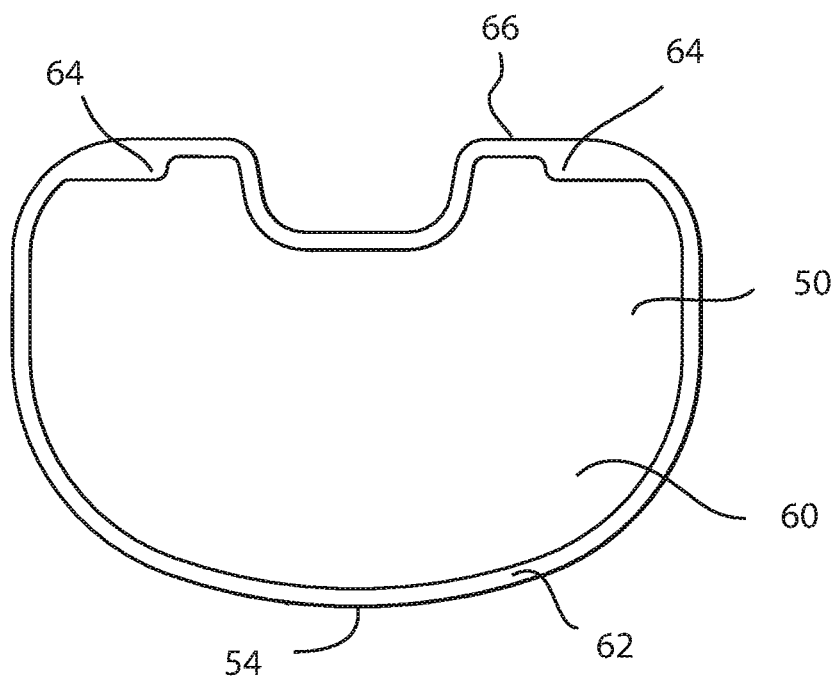
FIG. 3B is a top view of the tibial component of FIG. 1.
Figure 4:
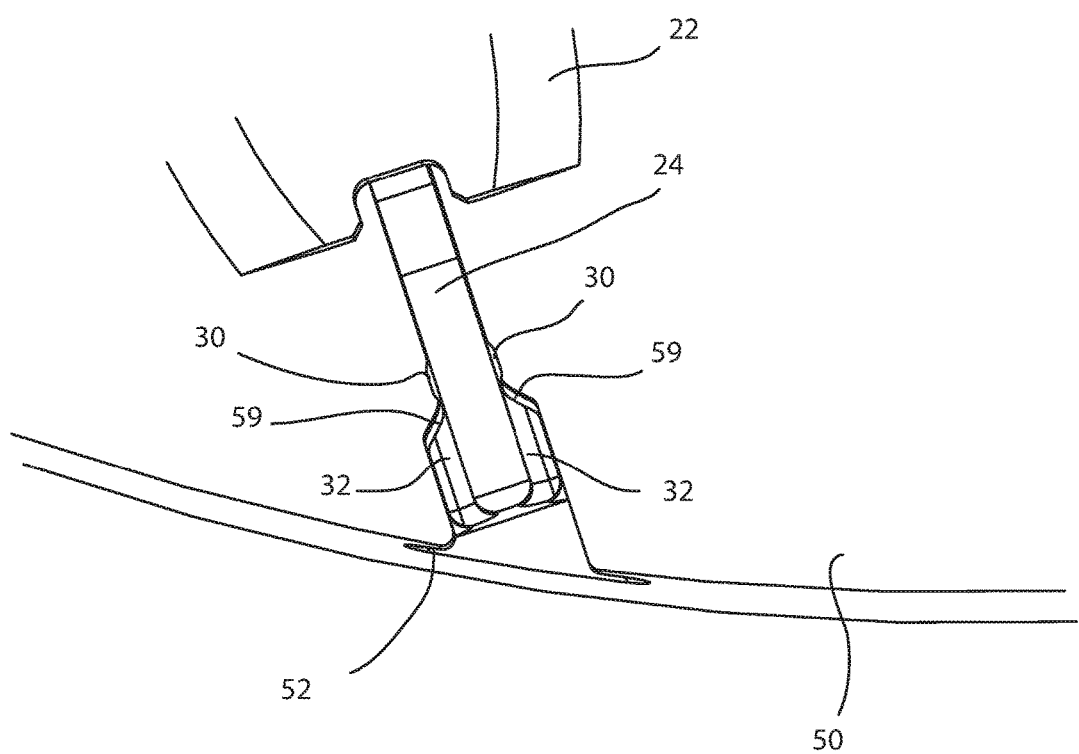
FIG. 4 is a bottom detail view of a portion of the knee tibial prosthesis of FIG. 1.

Referring to FIGS. 3A and 3B, the tibial tray 50 includes a bone-contacting, or inferior side 56 across which the channels 52 are recessed. At one end of each channel 52, shoulders 59 are formed in the edges of the channels 52. In FIGS. 3A and 3B, the shoulders 59 are formed in interior edges of the channel near the anterior edge 54 of the tibial tray 50. As seen in FIG. 4, when the anchor rails 24 are inserted through the channels, the shoulders 59 deform the tabs 30 and engage with the stops 32 to provide the interference fit between the anchors 20 and the tray 50, and to properly position the anchors at the correct depth relative to the tray. A stem 58 provides further fixation of the tray 50 in the tibia.

The tibial tray 50 further includes a joint-facing, or superior side 60 to which an articular insert (not shown) may be mounted. A raised rim 62 encompasses the superior side 60, and overhangs 64 are formed on a portion of the rim 62 for engagement with an articular insert and/or instruments. Tibial tray 50 may be described as a bicondylar tibial component because it is adapted to extend across an entire resected tibial plateau to replace the medial and lateral condyles.

In other embodiments, the features of the tibial tray 50 may vary. For example, the stem 58 or other fixation features may vary; the size and thickness of the tray 50 may vary, the outer peripheral size and shape may vary. Different connection features for engagement with an articular insert may be incorporated. Other features of tibial trays known in the art may be included as desired. The articular insert may carry the prosthetic articular surface.

Figure 5A:
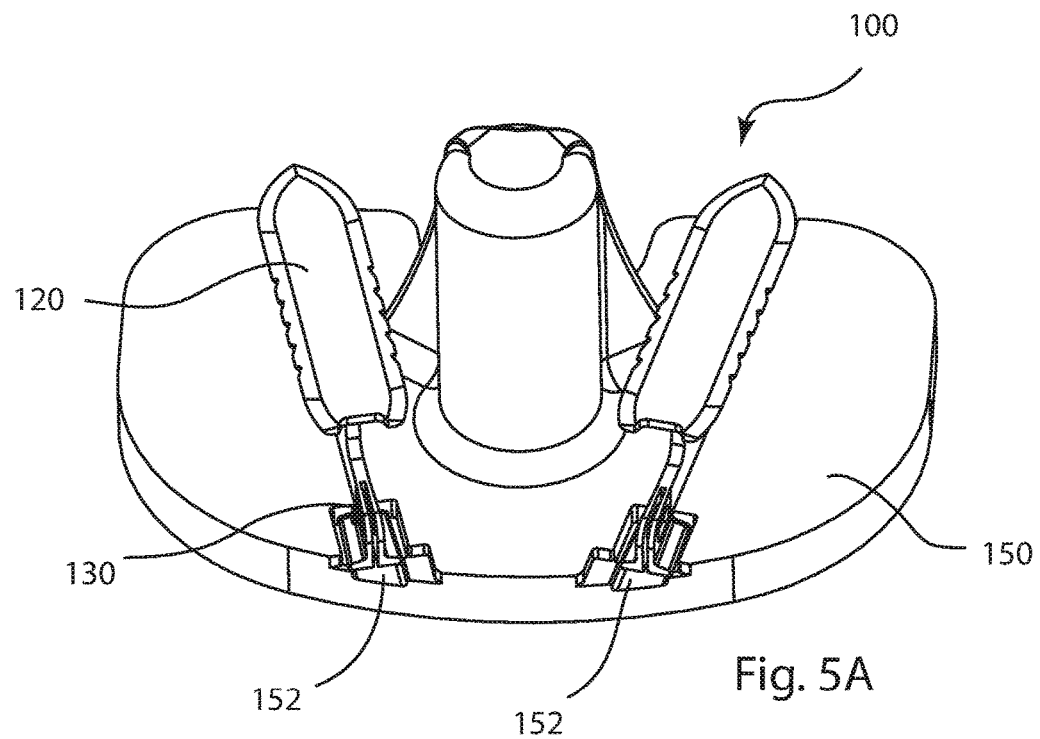
FIG. 5A is a bottom perspective view of another knee tibial prosthesis with a bicondylar tibial component and fixation elements.
Figure 5B:
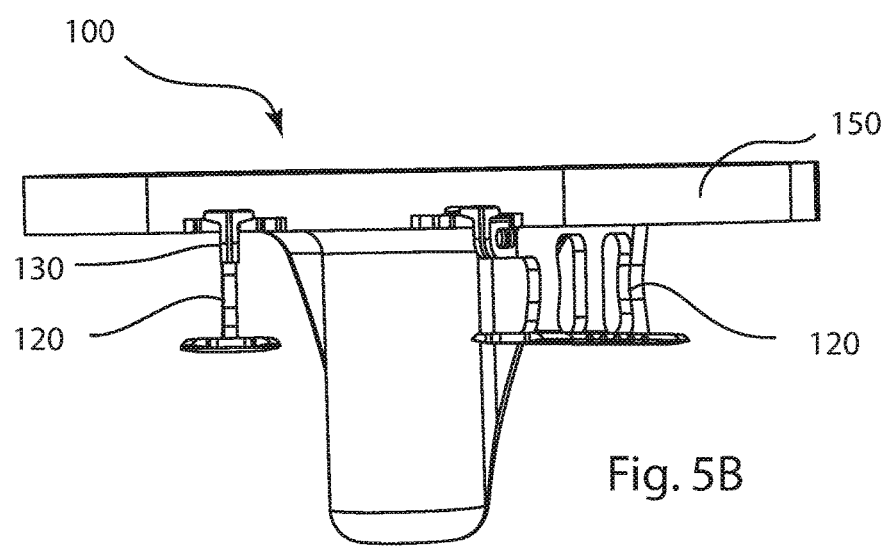
FIG. 5B is a front oblique view of the knee tibial prosthesis of FIG. 5A.

FIGS. 5A and 5B depict another example of a knee tibial prosthesis 100 which includes a tibial component 150, or tray 150, and at least one fixation element 120. Except for differences in channels for receiving the anchors, tibial tray 150 may be essentially identical to tray 50 and as such will not be further described. Similarly, the anchors 120 may be identical to anchors 20, with the exception of a spring feature 125 which may substitute for the tabs 30 and stops 32 formed on anchor 20.

Figure 6A:
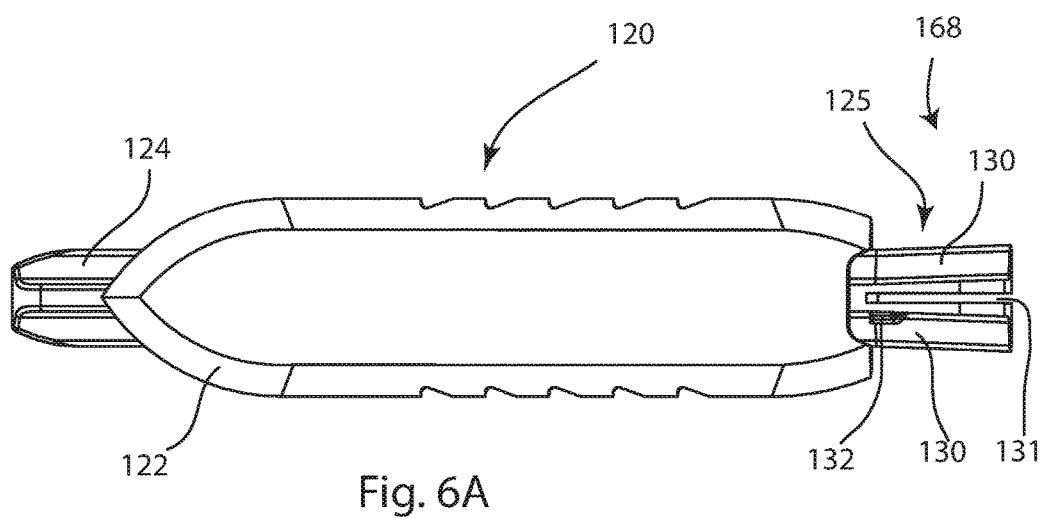
FIG. 6A is a top view of one of the fixation elements of FIG. 5A.
Figure 6B:
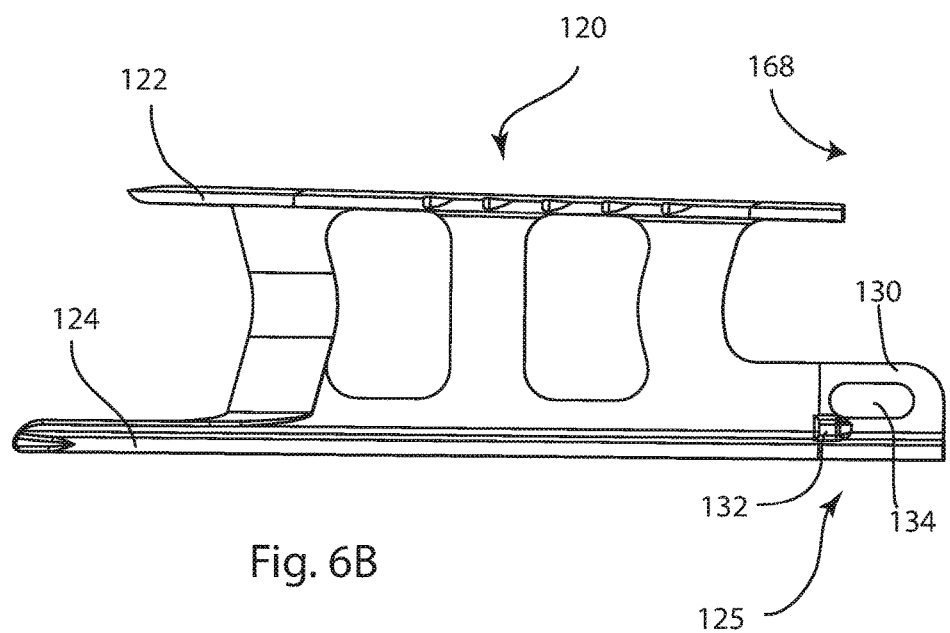
FIG. 6B is a side view of the fixation element of FIG. 6A.

Referring to FIGS. 6A and 6B, anchor 120 includes blade 122 and rail 124. Spring feature 125 is formed on the rail, and comprises a pair of tabs 130 separated by a gap 131. The spring feature 125 may be located at a proximal end 168 of the anchor 120, which may also be called a trailing end 168. A stop 132 may be formed on the rail. The stop 132 may be on a tab 130, as shown, or elsewhere. An opening 134 may be formed through the tabs 130 to provide a connection feature for anchor insertion and/or removal instruments.

Figure 7:
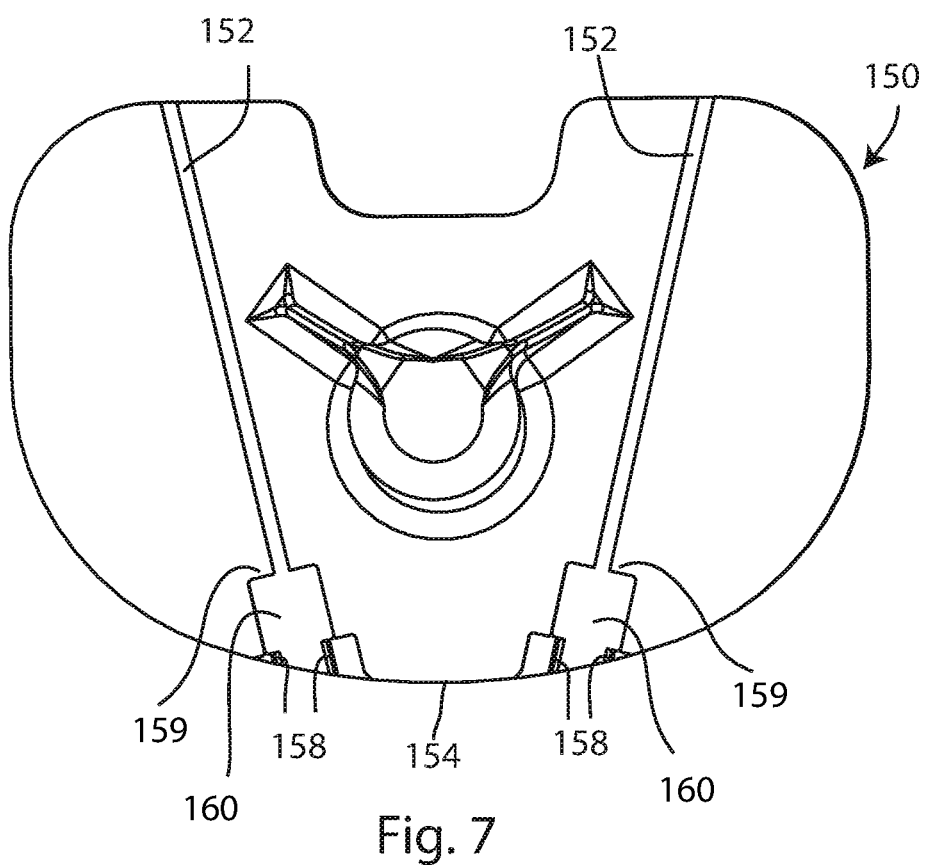
FIG. 7 is a bottom view of the tibial component of FIG. 5A.

Referring to FIG. 7, tray 150 includes channels 152 for receiving anchors 120. Curbs 158 may be present on either side of the channel 152, the curbs effectively narrowing a portion of the channel. Curbs 158 are illustrated near an anterior edge 154 of the tibial tray 150, but may be located elsewhere along the channel. Shoulders 159 may also be located on either side of the channel 152, and may be distal to, or posterior to, the curbs 158. A clearance pocket 160 may be defined along a portion of the channel 152 bounded by the shoulders 159 at one end and the curbs 158 at the other end.

Figure 8A:
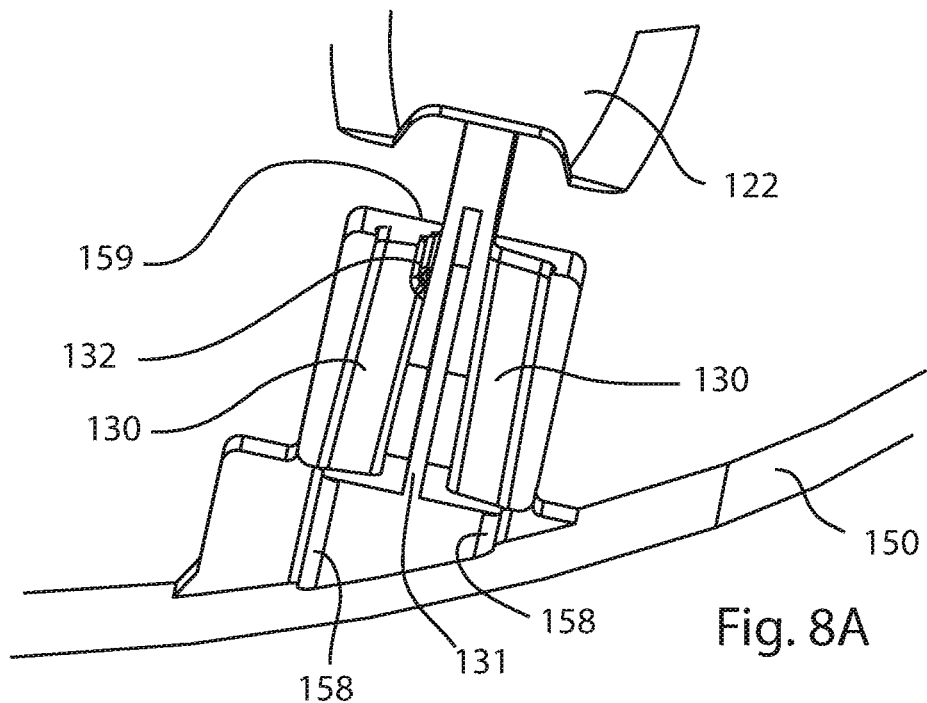
FIG. 8A is a bottom detail view of a portion of the knee tibial prosthesis of FIG. 5A.
Figure 8B:
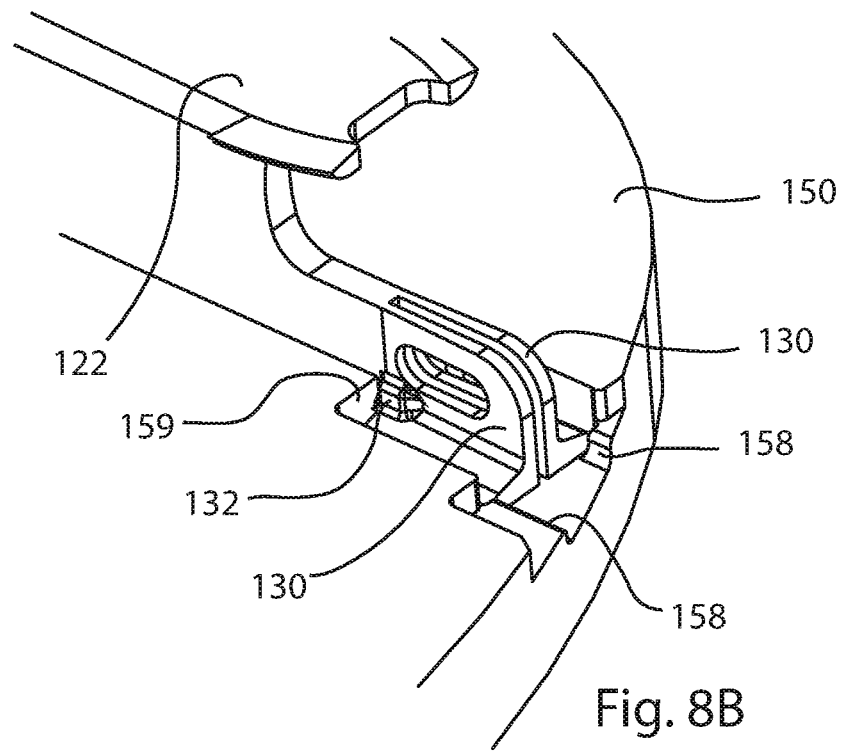
FIG. 8B is a bottom perspective detail view of the portion of the knee tibial prosthesis of FIG. 5A.

Referring to FIGS. 8A and 8B, as anchor 120 is inserted into channel 152, tabs 130 are compressed together, narrowing gap 131, as they pass between curbs 158. Once the tabs 130 are distal to the curbs, the tabs spring apart in the clearance pocket 160. Stop 132 engages with shoulder 159 to prevent further insertion of the anchor 120 distally. The stop 132 near the proximal anchor end 168 may be said to index to shoulder 159, which may be a flat face of the tibial tray 150, to prevent the anchor from being over-driven. Also, tabs 130 engage with curbs 158 to prevent proximal withdrawal of the anchor 120 from the tibial tray 150. The spring feature 125 prevents the anchor 120 from backing out proximally until the spring is depressed. If removal of an anchor is desired, an instrument (not shown) may be engaged with the tabs 130 to compress the tabs together and allow proximal withdrawal of the anchor.

To achieve optimal compression between the bone and the tibial tray, the anchor blade 122 may be angled divergent from the rail 124, in the same manner as described for anchor 20.

Figure 9A:
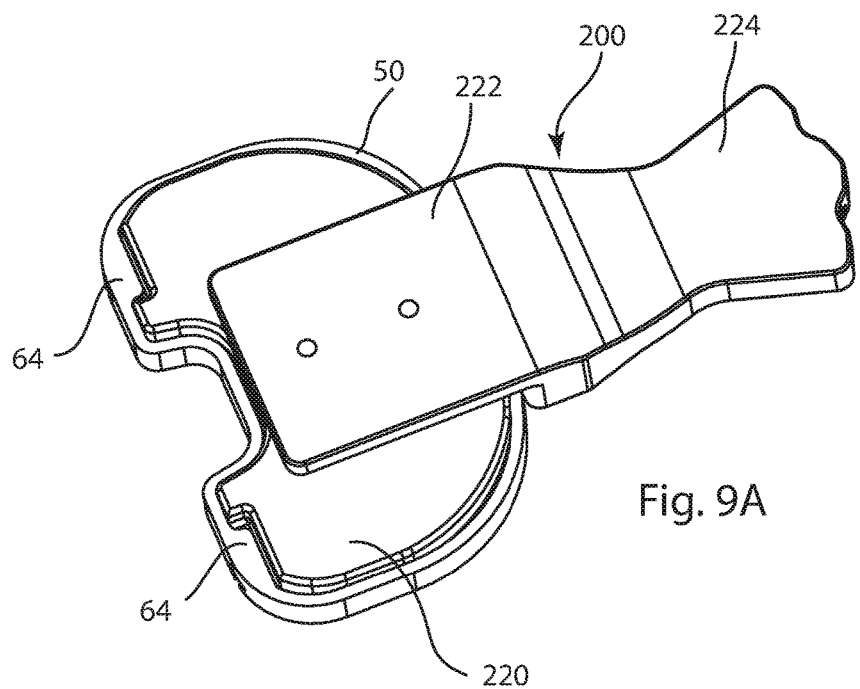
FIG. 9A is a top perspective view of the tibial component of FIG. 1 engaged with a fixation element guide instrument, a portion of the instrument not shown.
Figure 9B:
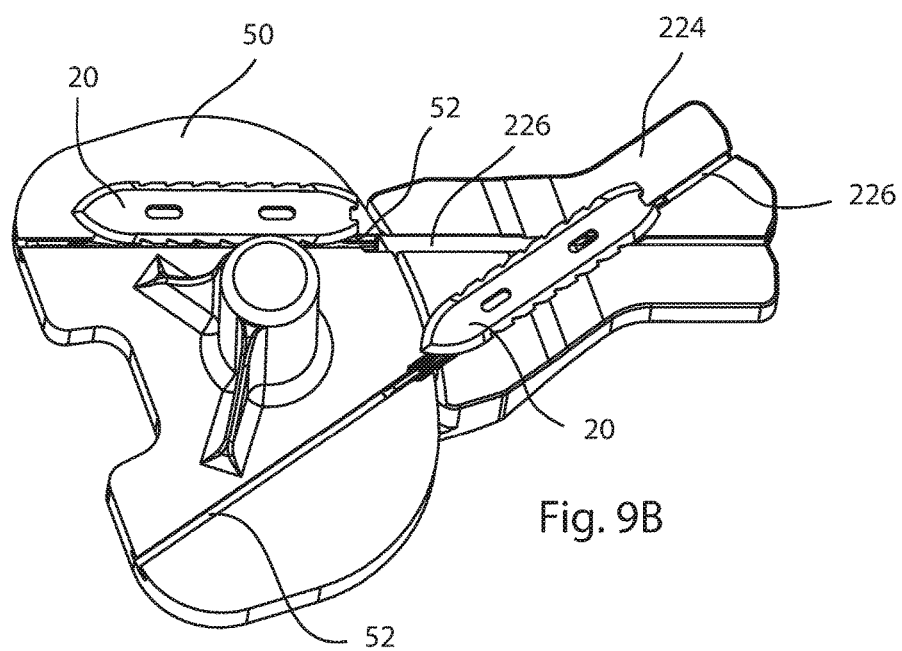
FIG. 9B is a bottom perspective view of the tibial component and instrument of FIG. 9A engaged with the fixation elements of FIG. 1, a portion of the instrument not shown.

Referring to FIGS. 9A and 9B, an anchor guide instrument 200 may be used to provide guidance as the anchors slide into the channels on the tibial tray. The example shown depicts anchors 20 being inserted into tray 50; however the same instrumentation with little or no modification may be implemented with tray 150 and anchors 120.

The anchor guide instrument 200 can attach to a polymeric (UHMW or other medically relevant polymer) clip 220 that interfaces via a snap fit to the superior surface 60 of the tibial tray 50. The clip 220 may engage with the overhangs 64 on the tray to snap to the tray 50, similar to the manner in which the articular insert attaches to the tray. The anchor guide instrument 200 includes an attachment portion 222 and a guidance portion 224. The guidance portion 224 includes two tracks 226, which coaxially align with the channels 52 on the tray 50 when the anchor guide instrument 200 is properly attached to the tray 50. Each anchor 20 may then be inserted into a track 226 and moved distally along the track until the anchor slides into channel 52. An insertion instrument may be used to tap or otherwise urge the anchor along the track and into the channel.

In a method of use, a tibia proximal end is prepared to receive tray 50 or 150. A transverse resection may be made to remove the medial and lateral proximal tibial articular cartilage. Recesses for a tray stem 58 and/or fins may be reamed, drilled, broached, cut or otherwise prepared. Tray 50 or 150 is fit onto the prepared tibia, and may be implanted with or without cement. Anchors 20 or 120 are inserted into the channels on the tray. The blades may cut into the bone as the anchors are inserted. As the anchors are inserted, the angled configuration of the anchors causes compression of the tray toward the tibia; i.e., the tray is pulled toward the tibia. The tabs and stops on the tray and the anchors cooperate to seat the anchors at the proper depth relative to the tray, and prevent unintentional withdrawal of the anchors. An articular insert (not shown) may be coupled to the superior surface of the tray 50, and may include an articular surface.

Referring to FIG. 2B, it can be appreciated that the act of inserting anchor 20 into channel 52 and adjacent bone may be described as a sequence of events. The leading end 70 is configured so that the rail 24 is the leading feature, and is thus the first feature to engage the channel or bone. The blade 22 is the second feature to engage, as its point penetrates the bone. The support 26 is the third feature to engage, as it enters the channel and the bone. The support may be said to protrude through the bone-contacting surface, since the support extends through the open side of the channel. All leading edges of the support and blade are sharpened and obliquely oriented to reduce the effort necessary to cut through the bone.

Any of the embodiments described herein may be used in a tibial prosthesis implantation procedure to provide immediate and tight fixation of the tibial component to the prepared tibia. The angled anchor blades provide immediate compression between the tibial component and the tibia as the anchors are inserted, and may provide complete fixation (no motion permitted between the tibial component and the tibia) for the time needed for bone ingrowth to occur between the tibia and the tibial component.

Any of the tibial trays and anchors described herein may be formed of titanium, cobalt chrome, stainless steel, or other biocompatible metals or metal alloys, or a combination thereof. In some embodiments, the anchors may be formed of a resorbable material such as PLLA. Any of the components may include a coating or treatment on part of or the entire component to promote biologic/bone ingrowth.

In other embodiments, another joint replacement component may have the channels as described above for anchoring the component to bone with the anchors disclosed herein. For example, the channels and anchors described herein may be applied to a femoral component of a knee replacement prosthesis, a stem and/or cup component of a hip or shoulder prosthesis, ankle prostheses, elbow prostheses, or small joint prostheses. Application to all synovial joints of the body is contemplated.

Referring to FIGS. 10-12B, another knee tibial prosthesis 320 includes a unicompartmental tibial component 310 and at least one fixation element 350. In this example the fixation element may be inserted from an anterior edge of the tibial tray 310 and may run roughly anterior-posterior. However, various anchor insertion angles are contemplated.

Figure 10:
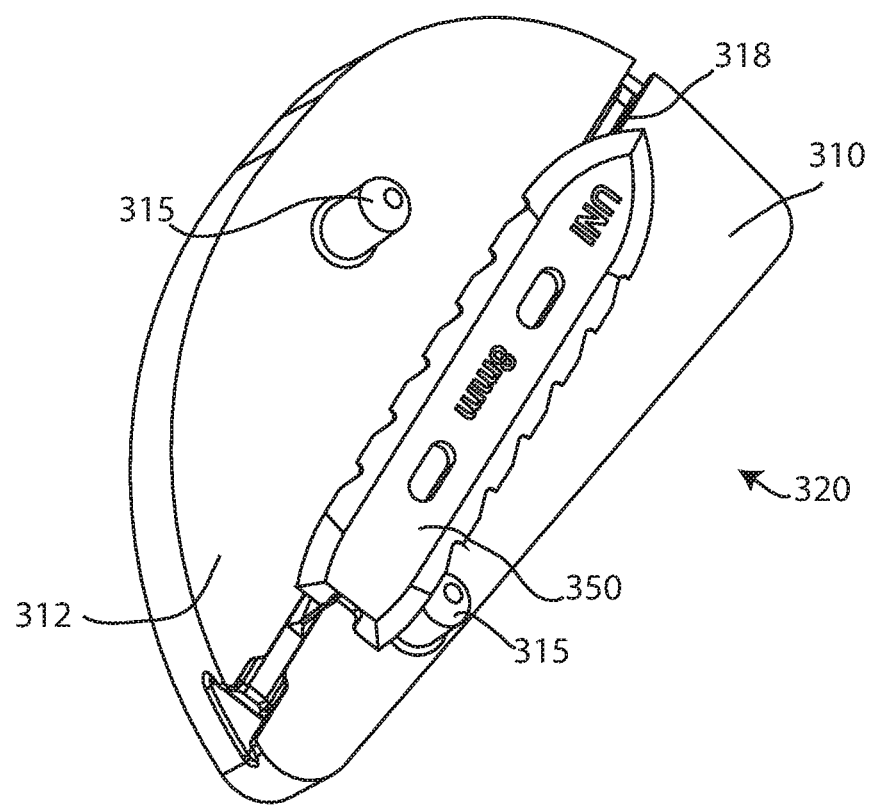
FIG. 10 is a bottom perspective view of yet another knee tibial prosthesis with a unicondylar tibial component and a fixation element.

The tibial component, or tray 310 may include an inferior or bone-contacting surface 312 and a joint-facing, or superior surface 314. The bone-contacting surface 312 may include at least one anti-rotation post 315. FIG. 10 shows an example with two posts 315. Other elements, such as fins, pegs, screws, or the like may be present as well. The posts 315, when embedded in the bone, may prevent the tibial component 310 from rotating on the flat resected bone surface. The bone-contacting surface 312 also includes at least one track 318. The track 318 is shaped to accept a complementary portion of the anchor 350. The track and anchor portion may be any complementary guiding features, such as dovetail, T-shape, H-shape, or complementary curved features, among others. The track may be at least partially undercut in order to retain the anchor in the tibial component 310.

The joint-facing surface 314 includes a negative feature, or recess 322. This feature may receive an articular insert (not shown), and may also engage an anchor guide instrument. There may be an undercut flange 324 on a posterior side 326 of the tibial component 310, under which the articular insert or instrument snaps to be held rigidly in the tray 310. In other embodiments, the superior surface 314 may be an integral articular or bearing surface configured to replicate a removed natural articular surface, and thus configured to contact and articulate with a natural distal femur, for a hemi-arthroplasty.

Figure 11A:
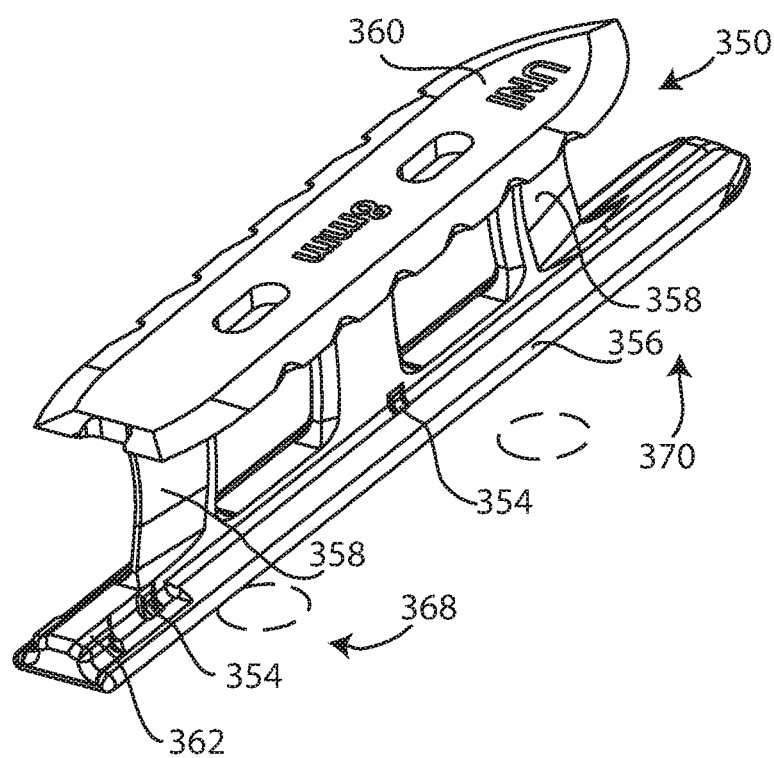
FIG. 11A is a side perspective view of the fixation element of FIG. 10.
Figure 11B:
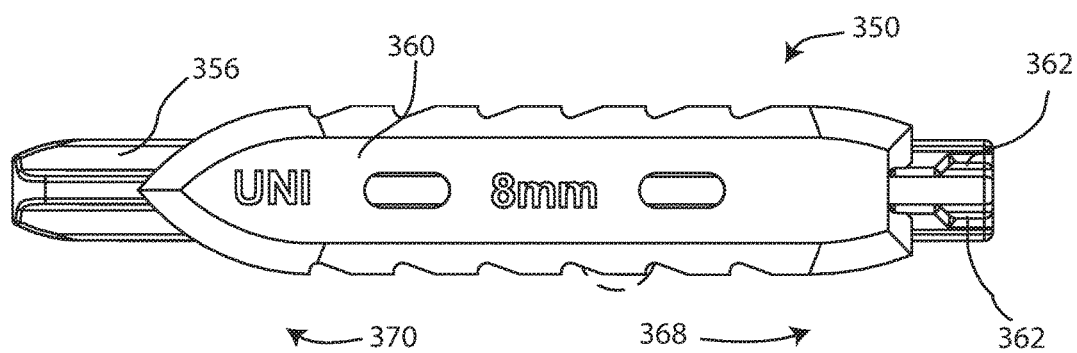
FIG. 11B is a top view of the fixation element of FIG. 10.
Figure 12A:
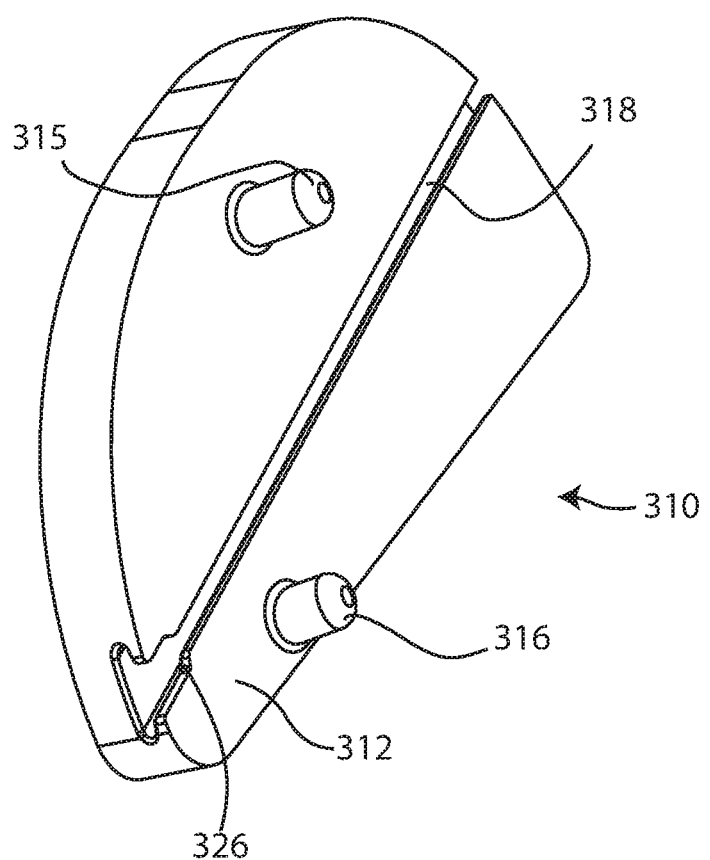
FIG. 12A is a bottom perspective view of the tibial component of FIG. 10.
Figure 12B:
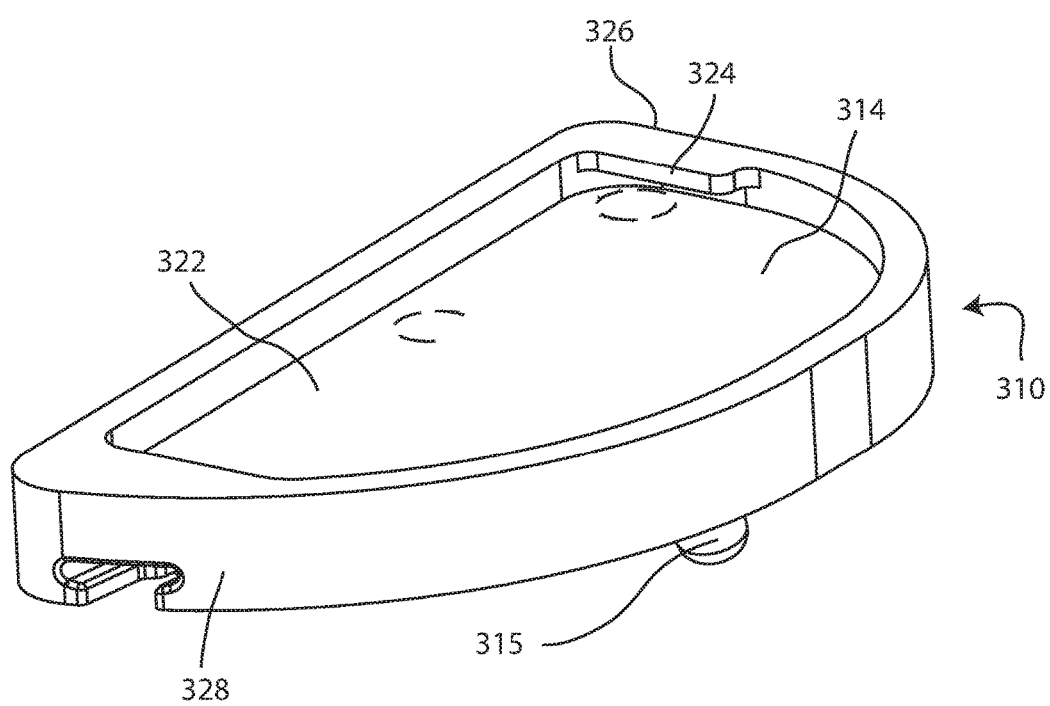
FIG. 12B is a top perspective view of the tibial component of FIG. 10.

Referring to FIGS. 10-11B, the anchors 350 are designed to slide into the bone. The anchors may be pushed or impacted into the bone. The anchor may include a longitudinal rail 356, at least one support 358, and a blade 360. The rail 356 is complementary to the track 318, and may therefore be a dovetail, T-shape, H-shape, or complementary curved feature, among others. There may be at least one interference tab 354 on the rail 356. The tab 354 deforms as the anchor 350 is driven into the track 318. This material deformation serves to take up any relative motion between the anchor 350 and the tibial tray 310 as well as to lock the anchor into the tray. In the example shown, a pair of tabs 354 is near a trailing end 368 of the anchor 350, and another pair of tabs 354 is centrally located along the rail. Other embodiments may include multiple interference tabs 354 along the length of the rail 318. The trailing end 368 may also be described as the proximal end 368. The anchor 350 also has an opposite leading end, or distal end 370. There may be a physical stop tab 362 on the rail. The stop tab 362 is shown immediately proximal to the interference tab 354, although other locations are contemplated. As the rail 356 is inserted in the track 318, the stop tab 362 may approach a matching stop feature 326 on the tray 310 which prevents insertion of the anchor 350 beyond a prescribed point.

To achieve optimal compression between the bone and the tibial tray 310, the anchor blade 360 may diverge from the rail 318 and/or the bone-contacting surface 312 as described for tibial prosthesis 10.

Figure 13A:
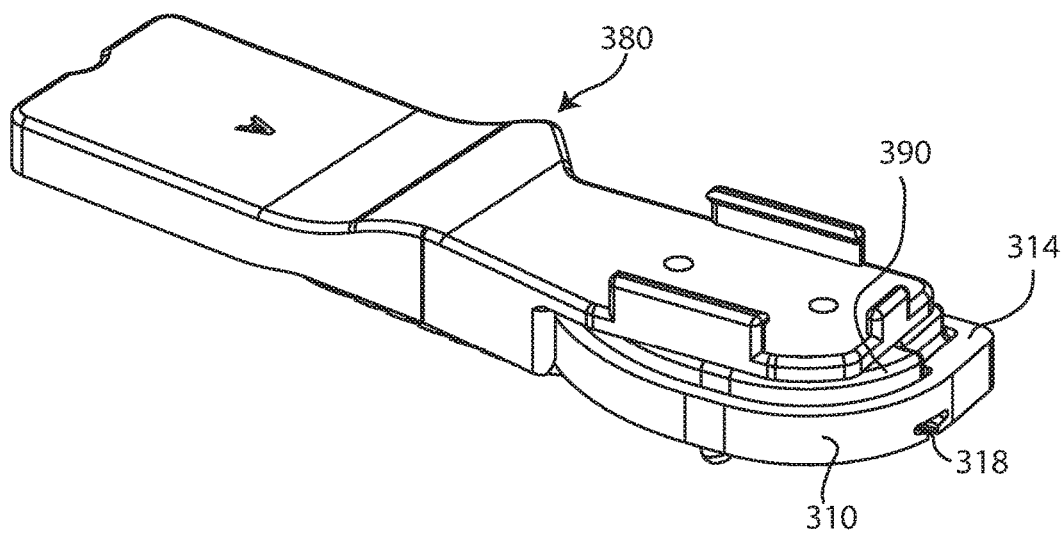
FIG. 13A is a top perspective view of the tibial component of FIG. 10 engaged with a fixation element guide instrument.
Figure 13B:
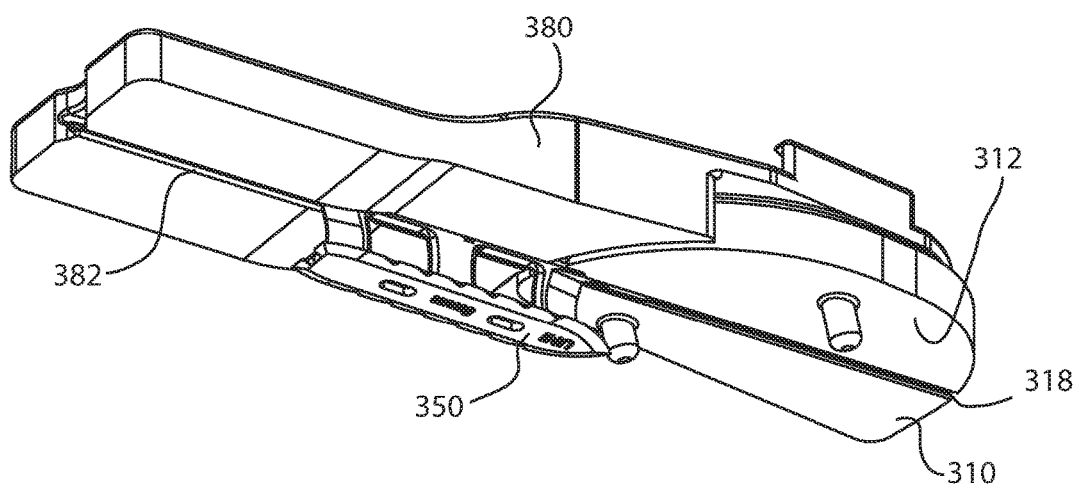
FIG. 13B is a bottom perspective view of the tibial component and instrument of FIG. 13A engaged with the fixation element of FIG. 10.

Referring to FIGS. 13A and 13B, during implantation the anchors 350 may be guided into the appropriate tracks 318 via an anchor guide instrument 380. The anchor guide 380 may attach to an anchor guide clip 390. The clip 390 may include an engagement feature which releasably connects to the anchor guide. The clip may also snap into the recess 322 on the tibial tray 310 and under the flanges 324, as would an articular insert. The clip 390 may be ultra-high molecular weight polyethylene (UHMWPE) or other medically relevant polymer. The anchor guide 380 includes a track 382 which coaxially aligns with track 318 on the tray 310. An anchor 350 may be inserted at the free end of track 382, urged distally along track 382 toward the tray 310 and into track 318 on the tray. A mallet or other instrument may be used to drive the anchor into the bone material adjacent the tibial component.

Another example of a knee tibial prosthesis may include a unicompartmental tibial tray with a plurality of tracks 318, into which a plurality of anchors 350 may be inserted. More than one anchor may be inserted per track. Although track 318 is illustrated in FIG. 10 as extending generally anterior-posterior (A/P), it is appreciated that in other embodiments the track may extend generally medial-lateral (M/L), or along any vector between the A/P and L/M directions. Furthermore, the track 318 may diverge from the bone-contacting surface 312.

A knee femoral component includes at least one groove or track for engagement of an anchor which may slide into the groove and into an adjacent distal femur to anchor the femoral component to the distal femur. The femoral component may be a unicondylar or bicondylar femoral component. Anchors may be driven into grooves in the femoral component at any location to provide fixation and/or compression of the femoral component surface against the bone.

Figure 14:
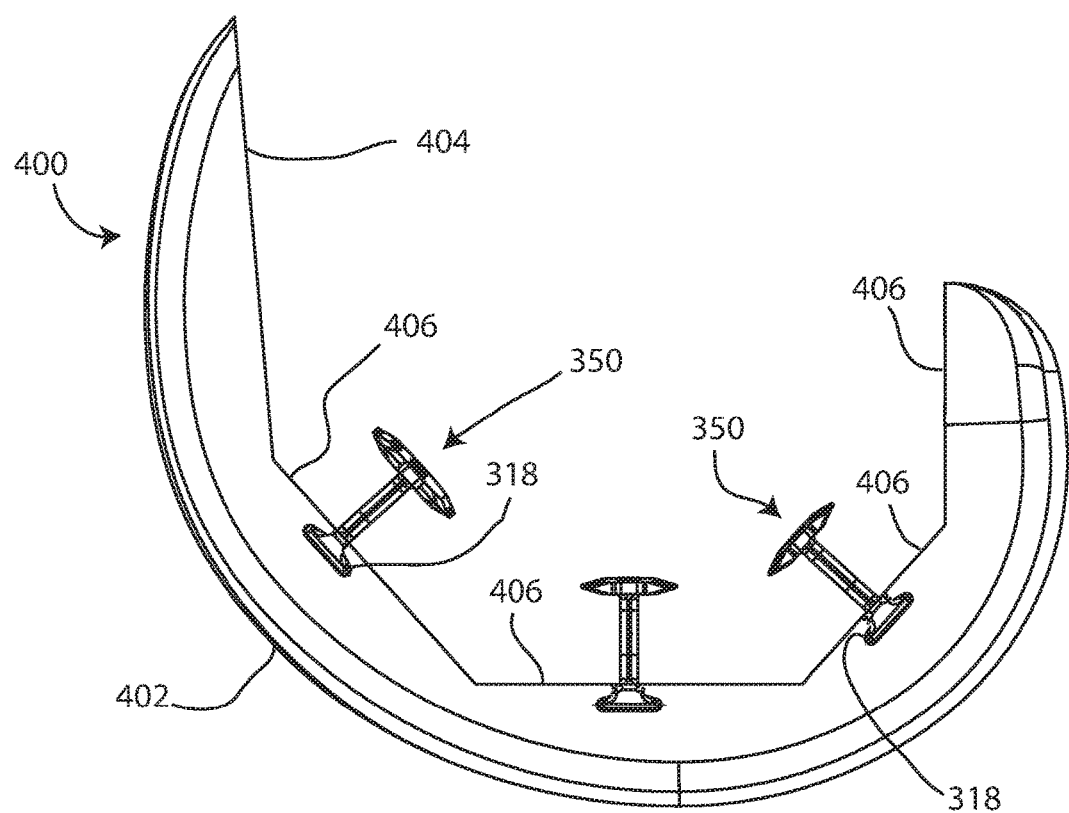
FIG. 14 is a side view of a knee femoral prosthesis with a bicondylar femoral component and fixation elements.

Referring to FIG. 14, a knee femoral prosthesis 400 includes an outer bearing surface 402 and an inner fixation surface 404. The bearing surface 402 may also be called an articular surface or a joint-facing surface. The inner fixation surface 404 may also be called a bone-contacting surface. The fixation surface 404 may include multiple segments 406. Each inner surface segment 406 may be aligned along a different plane, or may be coplanar with at least one other segment. At least one segment 406 includes a track 318 shaped to hold an anchor 350 as described above. The track(s) 318 may run medial-lateral across the inner fixation surface 404 as shown in FIG. 14, although other trajectories are envisioned, such as anterior-posterior, superior-inferior, or along an intermediate trajectory. The anchors 350 may be driven into the tracks 18, providing fixation and/or compression of the femoral component to the bone.

Figure 15:
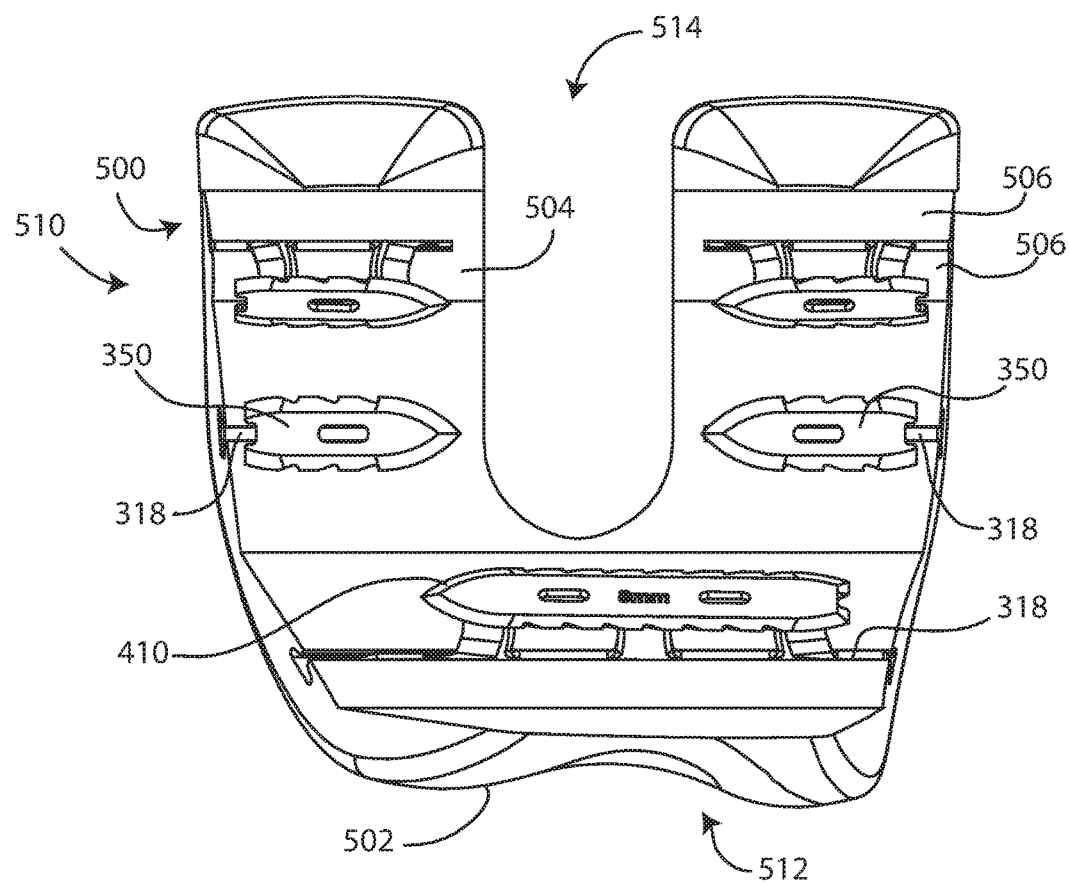
FIG. 15 is a top view of another knee femoral prosthesis with a bicondylar femoral component and fixation elements.

FIG. 15 shows a top-down view of another knee femoral prosthesis 500 which includes a femoral component 510 and at least one anchor 350. The femoral component 510 includes an outer bearing surface 502 and an inner fixation surface 504. The bearing surface 502 may also be called an articular surface or a joint-facing surface. The inner fixation surface 504 may also be called a bone-contacting surface. Component 510 includes at least one track 318. In this example, two tracks 318 extend medial-lateral across the fixation surface 504. Two anchors 350 are shown engaged in one of the tracks 318 toward a posterior aspect 514 of the femoral component 510. In other embodiments, three anchors 350 could be engaged in the posterior track 318. The anchors 350 may be inserted from either or both of the medial or lateral sides of the implant. The prosthesis 500 also includes an elongated anchor 410 engaged in the other track 318 toward an anterior aspect 512 of the femoral component 510. In other embodiments, multiple anchors 350 could be used in place of the elongated anchor 410, and vice versa. In other embodiments, the tracks and anchors may be angled relative to the medial-lateral dimension of the femoral component, and may be inserted from any edge, whether medial, lateral, anterior, posterior, or intermediate. The length, width, height, and/or other dimensions of the anchor 350, 410 may be appropriately scaled for the selected placement location on the component and the adjacent bone portion.

Figure 16A:
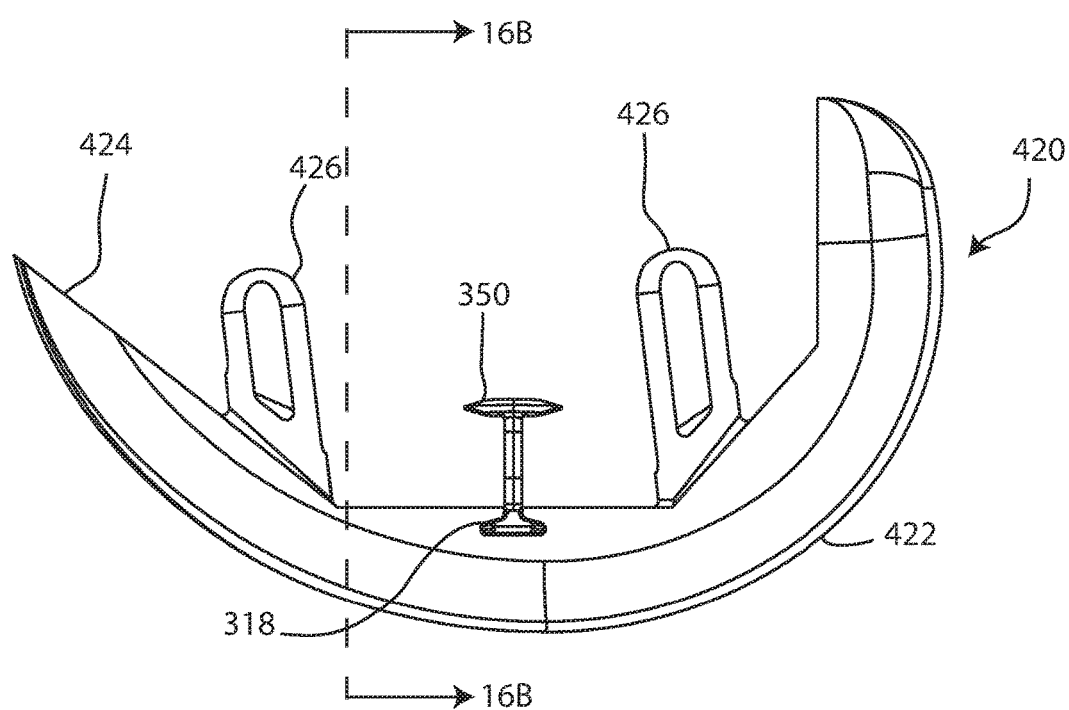
FIG. 16A is a side view of yet another knee femoral prosthesis with a unicondylar femoral component and a fixation element.
Figure 16B:
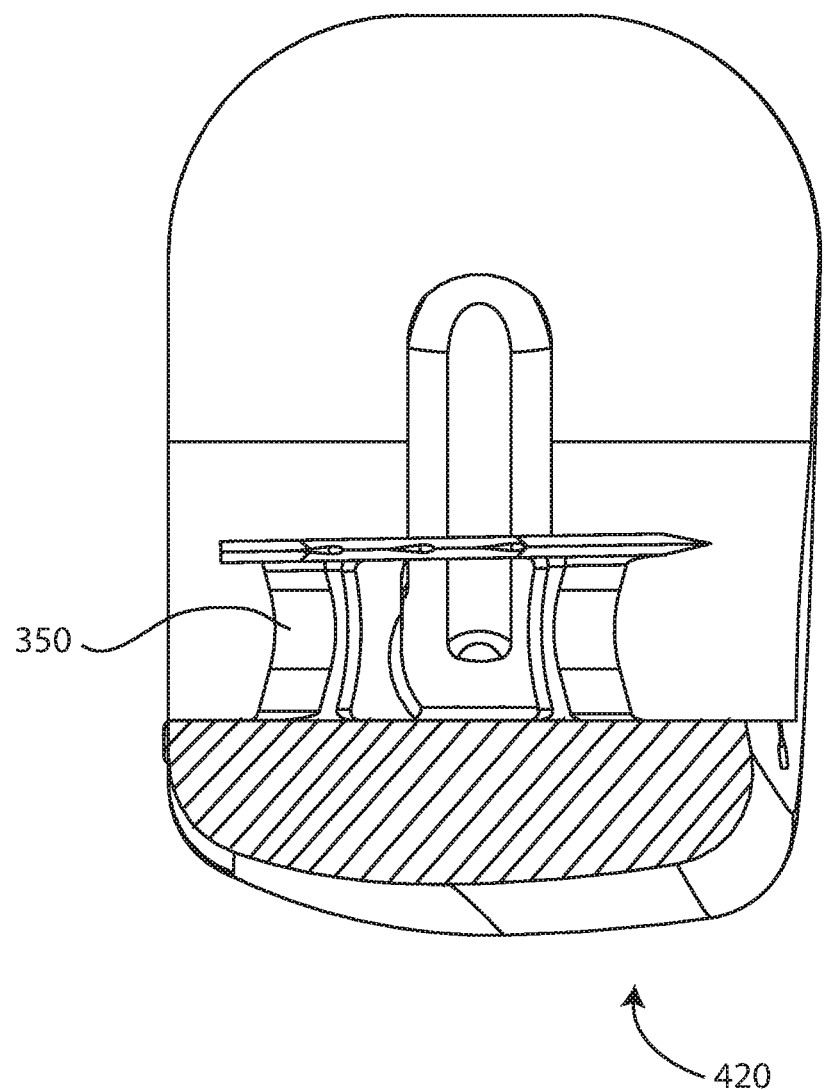
FIG. 16B is a front cross section view of the knee femoral prosthesis of FIG. 16A sectioned along line 16B-16B of FIG. 16A.

Referring to FIGS. 16A and 16B, lateral and anterior views of a unicondylar knee femoral prosthesis 418 are shown. Prosthesis 418 includes a unicondylar femoral component 420 and at least one fixation element 350. Femoral component 420 includes an outer bearing surface 422 and an inner fixation surface 424. The bearing surface 422 may also be called an articular surface or a joint-facing surface. The inner fixation surface 424 may also be called a bone-contacting surface. At least one anchor peg 426 may protrude from the inner fixation surface 424. The illustrated example shows two pegs. The anchor 350 is engaged in a tapered dovetail track 318 on the inner fixation surface 424 to provide fixation and compression of the femoral component 420 against the bone. Although one fixation anchor 350 is shown, in other embodiments multiple fixation anchors 350 may be engaged in one or more tracks 318. The anchor 350 may be inserted into the track 318 and the adjacent bone from the lateral or medial side of the femoral component 420.

A tibial hemiarthroplasty component includes at least one groove or track for engagement of an anchor which may slide into the groove and into an adjacent proximal tibia to anchor the component to the proximal tibia.

Figure 17A:
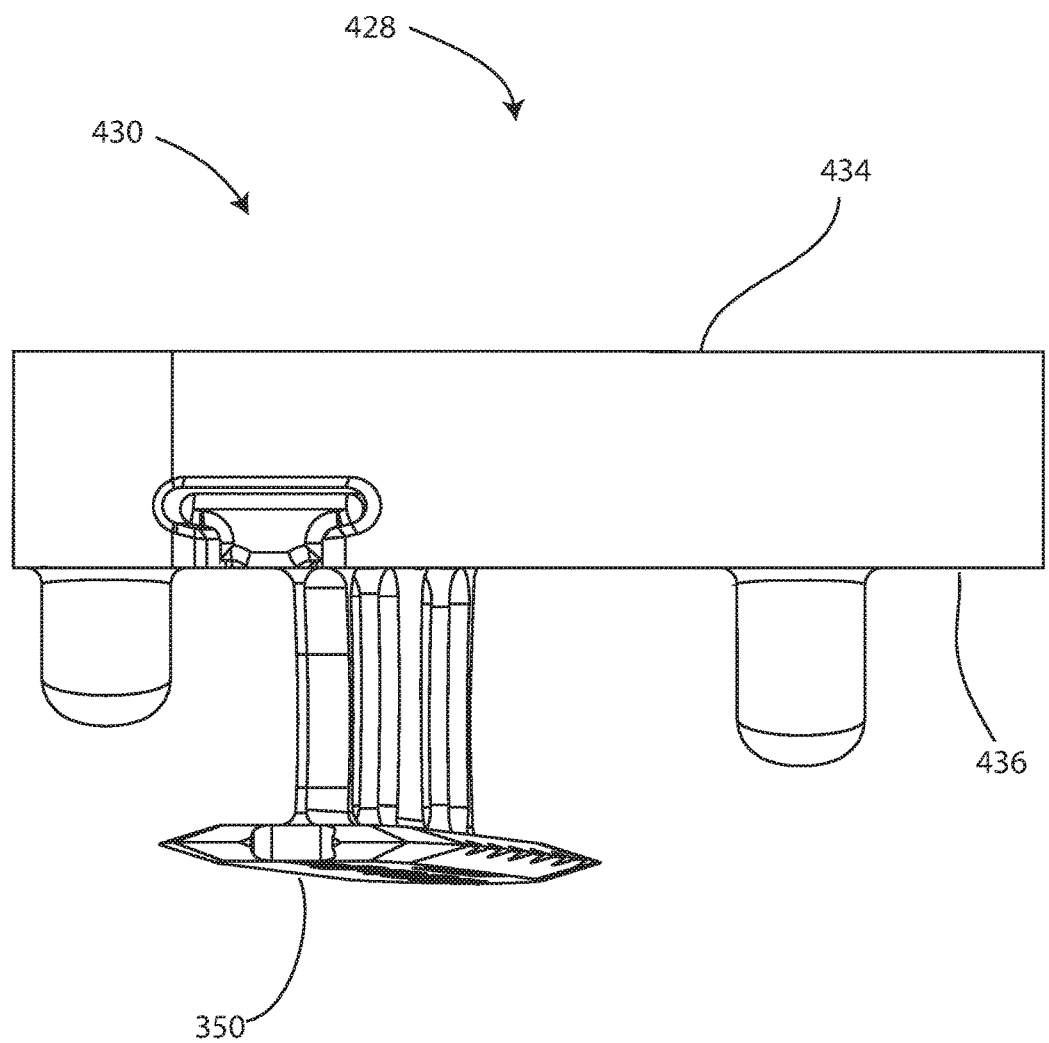
FIG. 17A is a front view of another knee tibial prosthesis with a unicondylar hemiarthroplasty tibial component and a fixation element.
Figure 17B:
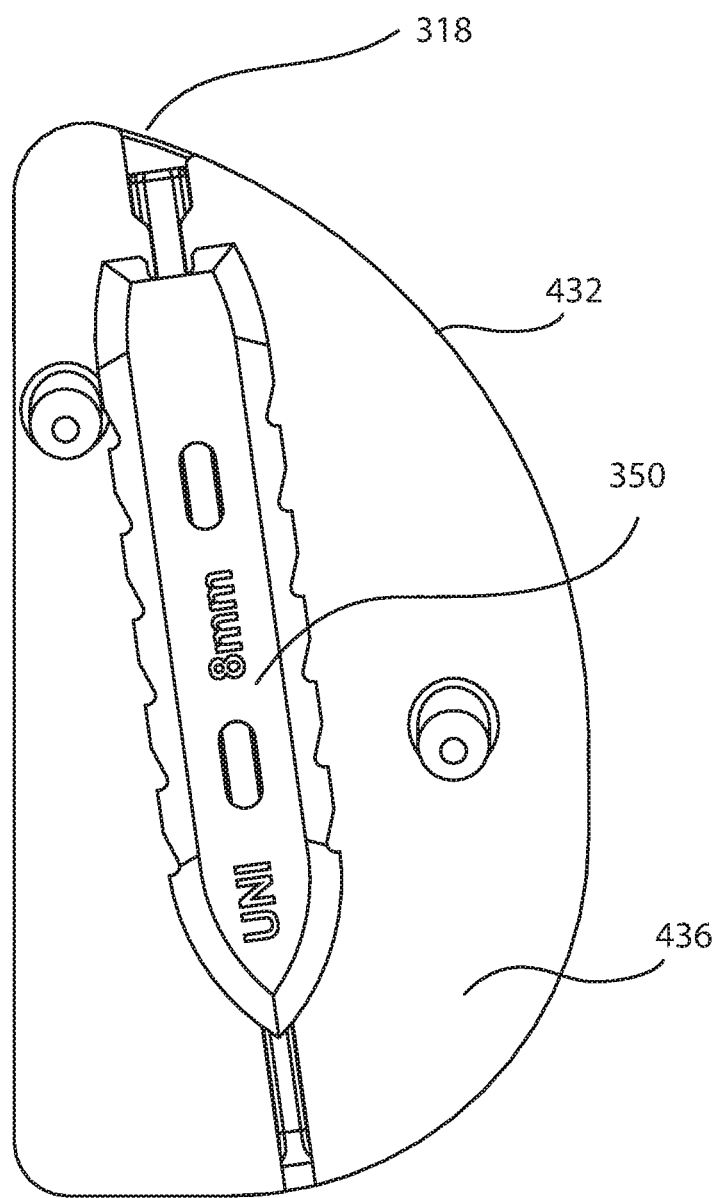
FIG. 17B is a bottom view of the knee tibial prosthesis of FIG. 17A.

Referring to FIGS. 17A and 17B, a unicondylar hemiarthroplasty knee tibial prosthesis 428 is shown. The prosthesis 428 includes a tibial component 430 and at least one fixation element 350. The tibial component 430 includes a track 318 to receive an anchor 350. The track 318, anchor 350 and insertion techniques may be the same as those described above with regard to FIGS. 10-16B. The tibial component 130 has a superior side 434 and an inferior side 436. The superior side 434 may be metal and it may form a bearing surface for articulation with a natural distal femur. It is appreciated that as needed, a single hemi-arthroplasty component 430 may be implanted for a unilateral hemiarthroplasty, or two generally mirror-image components may be implanted for a bilateral hemiarthroplasty.

In any of the examples described above, the anchors may vary in geometry and angle (for compression). The anchors may be positioned anywhere along the relative implants, i.e. medial, lateral, anterior, posterior or intermediate. Also, the dovetail track could have a different geometry than a taper dovetail. The extent of compression achieved may be adjusted by varying the angle of the blade. Advantageously, use of the disclosed anchor may prevent osteolysis, as no pathway for osteolysis is provided, unlike in screw-based fixation systems. The number of anchors used in a track or implant may vary.

The present technology may be embodied in other specific forms without departing from its spirit or essential characteristics. It is appreciated that various features of the above described examples can be mixed and matched to form a variety of other alternatives. As such, the described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A joint arthroplasty system, comprising:
   a prosthetic articular surface which replaces at least a portion of a natural articular surface of a bone;
   a prosthetic component comprising a bone-contacting surface configured to compliment a resected or flattened bone surface, the bone-contacting surface comprising at least one undercut channel extending across at least a portion of the bone-contacting surface and through a perimeter edge of the bone-contacting surface; and
   an anchor comprising a rail, a blade, and a support, the rail comprising at least one lateral protrusion, the blade offset from the rail, the support connecting the rail and the blade;
   wherein the rail is insertable into the channel to connect the anchor to the prosthetic component;
   wherein, when the rail is inserted into the channel, the support protrudes through the bone-contacting surface, and the blade is carried at a distance from the bone-contacting surface, characterized in that the lateral protrusion is adapted such that, when the rail is inserted into the channel, the lateral protrusion plastically deforms to create an interference fit in the channel.

2. The system of claim 1, wherein the prosthetic component is selected from the group consisting of a knee tibial component, a knee femoral component, and a knee patellar component.

3. The system of claim 1, wherein the prosthetic articular surface is opposite the bone-contacting surface.

4. The system of claim 1, wherein the channel comprises at least one shoulder formed in an edge of the channel, wherein the shoulder deforms the lateral protrusion when the rail is inserted into the channel.

5. The system of claim 1, wherein the system is a knee arthroplasty system and wherein the prosthetic articular surface replaces at least a portion of a natural articular surface of a knee joint.

6. The system of claim 5, wherein the articular and bone-contacting surfaces are connected to a prosthesis selected from the group consisting of a knee tibial prosthesis, a knee femoral prosthesis, and a knee patellar prosthesis.

7. The system of claim 6, wherein the prosthesis is selected from the group consisting of a unicondylar prosthesis and a bicondylar prosthesis.

8. The system of claim 1, wherein a transverse cross section of the channel and a transverse cross section of the rail are complementary negative and positive dovetail shapes, respectively.

9. The system of claim 1, wherein the blade is inclined at an acute angle relative to the bone-contacting surface when the rail is in the channel.

10. The system of claim 1, wherein a leading end of the anchor includes oblique sharpened edges.

11. The system of claim 5, wherein, when the rail is inserted into the channel, the rail seizes in the channel.

12. A method of assembling a joint arthroplasty prosthesis for replacing at least a portion of a natural articular surface of a synovial joint, comprising:
- providing a prosthesis comprising a bone-contacting surface configured to compliment a resected or flattened bone surface and an articular surface, the bone-contacting surface comprising at least one undercut channel extending across at least a portion of the bone-contacting surface and through a perimeter edge of the bone-contacting surface, the articular surface replicating at least a portion of a natural articular surface of a synovial joint;
- providing an anchor comprising a rail, a blade, and a support, the rail comprising at least one laterally protruding tab, the blade offset from the rail, the support connecting the rail and the blade;
- sliding the rail into the channel, wherein the tab plastically deforms as the rail slides into the channel to create an interference fit in the channel; and
- sliding a portion of the support into the channel, the support protruding through the bone-contacting surface, wherein a portion of the bone-contacting surface is spaced between the blade and the rail when the rail and the support are in the channel.

13. The method of claim 12, wherein sliding the rail into the channel is performed before sliding the portion of the support into the channel.

14. The method of claim 12, wherein sliding the rail into the channel further comprises sliding the tab past a shoulder formed in an edge of the channel, wherein the shoulder deforms the tab.

15. The method of claim 12, wherein the blade is inclined at an acute angle relative to the bone-contacting surface when the rail is in the channel, wherein the acute angle opens toward a leading end of the anchor.

16. The method of claim 12, further comprising:
- providing a guide tool comprising an attachment portion and a guidance portion, the attachment portion releasably attachable to a portion of the prosthesis, the guidance portion including at least one track;
- attaching the attachment portion to the prosthesis, wherein the track coaxially aligns with the channel when the attachment portion is attached to the prosthesis;
- inserting the rail into the track; and
- sliding the anchor toward the prosthesis.

17. The method of claim 16, wherein attaching the attachment portion to the prosthesis comprises attaching a clip to the attachment portion and snapping the clip to the prosthesis.

* * * * *